United States Patent [19]

Skelly et al.

[11] Patent Number: 5,359,034
[45] Date of Patent: Oct. 25, 1994

[54] CYSTEINE DEPLETED IL-6 MUTEINS

[75] Inventors: Susan M. Skelly, Dunellen, N.J.; Charles T. Tackney, Brooklyn, N.Y.; John N. Snouwaert, Carrboro; Dana M. Fowlkes, Chapel Hill, both of N.C.

[73] Assignees: Imclone Systems Inc., New York, N.Y.; The University of North Carolina at Chapel Hill, Chapel Hill, N.C.

[21] Appl. No.: 907,710

[22] Filed: Jul. 2, 1992

Related U.S. Application Data

[63] Continuation-in-part of Ser. No. 724,698, Jul. 2, 1991, abandoned.

[51] Int. Cl.[5] .............................................. C07K 13/00
[52] U.S. Cl. ...................................... 530/351; 930/141; 424/85.2; 424/85.6
[58] Field of Search ........................ 530/351; 930/141; 435/69.52; 424/85.2, 85.6

[56] References Cited

U.S. PATENT DOCUMENTS 4,959,314  9/1990  Mark et al. ........................ 435/69.1

FOREIGN PATENT DOCUMENTS 0257406    3/1988  European Pat. Off. .
WO88/00206 1/1988  PCT Int'l Appl. .
WO90/06370 6/1990  PCT Int'l Appl. .

OTHER PUBLICATIONS

Jambou et al, PNAS 85, 1988, pp. 9426–9430.
Zhang et al, Eur. J. Biochem 207, 1992, pp. 903–913.
Simpson et al, Biochem Biophys. Res. Comm., 157(1) 1988, pp. 364–372.
Snouweart et al. JBC 266, 1991, pp. 23097–23102.
Snouwaert et al., Journal of Immunology 146, 585–591 (1991).
Brakenhoff et al., Journal of Immunology 145, 561–568 (1990).
Clogston et al., Archives of Biochemistry and Biophysics 272, 144–151 (1989).
Brakenhof et al., Journal of Immunology 143, 1175–1182 (1989).
Brakenhoff et al., Journal of Immunology 139, 4116–4121 (1987).
Asagoe et al., Biotechnology 6, 806–809 (1988).
Yasueda et al., Biotechnology 8, 1036–1040 (1990).
"Altered Sites in vitro Mutagenesis System Technical Manual," Promega Corporation.
Sugasarawa et al., Biotechnology 6, 895–902 (1988).

Primary Examiner—Garnette D. Draper
Attorney, Agent, or Firm—Irving N. Feit; Laura S. Weiss

[57] ABSTRACT

Muteins of IL-6 and truncated IL-6 are prepared by recombinant DNA techniques. In the muteins, the cysteine residues that occur at positions, or at positions corresponding to positions, 45 and 51 of mature, native IL-6 have been replaced by other amino acids. The cysteine residues that occur at positions, or at positions corresponding to positions, 74 and 84 are retained. The molecule has biological activity that is at least comparable to that of native IL-6.

10 Claims, 18 Drawing Sheets

```
GCT CCG GTT CCG CCA GGA GAA GAT TCC AAA GAT GTA GCC GCC CCA CAC   048
Ala Pro Val Pro Pro Gly Glu Asp Ser Lys Asp Val Ala Ala Pro His
 1           5                   10                  15

AGA CAG CCG CTC ACC TCT TCA GAA CGA ATC GAT AAA CAA ATT CGG TAC   096
Arg Gln Pro Leu Thr Ser Ser Glu Arg Ile Asp Lys Gln Ile Arg Tyr
            20                  25                  30

ATC CTC GAC GGG ATA TCA GCG CTG AGA AAA GAG ACC AGC AAC AAG AGT   144
Ile Leu Asp Gly Ile Ser Ala Leu Arg Lys Glu Thr Ser Asn Lys Ser
            35                  40                  45

AAC ATG AGC GAA AGC AGT AAA GAA GCA CTG GCA GAA AAC AAC CTG AAC   192
Asn Met Ser Glu Ser Ser Lys Glu Ala Leu Ala Glu Asn Asn Leu Asn
        50                  55                  60

CTT CCG AAG ATG GCT GAA AAA GAT GGA TGT TTT CAA TCT GGA TTC AAT   240
Leu Pro Lys Met Ala Glu Lys Asp Gly Cys Phe Gln Ser Gly Phe Asn
 65                 70                  75                  80

GAG GAA ACT TGT CTG GTG AAA ATC ATC ACA GGC CTT TTG GAA TTT GAG   288
Glu Glu Thr Cys Leu Val Lys Ile Ile Thr Gly Leu Leu Glu Phe Glu
                85                  90                  95

GTA TAC CTA GAG TAC CTC CAG AAC AGA TTT GAG AGT AGT GAG GAA CAA   336
Val Tyr Leu Glu Tyr Leu Gln Asn Arg Phe Glu Ser Ser Glu Glu Gln
                100                 105                 110

GCG AGA GCT GTC CAG ATG TCG ACC AAA GTC CTG ATC CAG TTT CTG CAG   384
Ala Arg Ala Val Gln Met Ser Thr Lys Val Leu Ile Gln Phe Leu Gln
            115                 120                 125

AAA AAG GCA AAA AAT CTA GAT GCA ATA ACC ACC CCG GAT CCA ACC ACA   432
Lys Lys Ala Lys Asn Leu Asp Ala Ile Thr Thr Pro Asp Pro Thr Thr
    130                 135                 140

AAT GCG AGC CTG CTG ACG AAG CTG CAG GCA CAG AAC CAG TGG CTG CAG   480
Asn Ala Ser Leu Leu Thr Lys Leu Gln Ala Gln Asn Gln Trp Leu Gln
145                 150                 155                 160

GAC ATG ACA ACT CAT CTC ATT CTG AGA TCT TTC AAA GAA TTC CTG CAG   528
Asp Met Thr Thr His Leu Ile Leu Arg Ser Phe Lys Glu Phe Leu Gln
                165                 170                 175

TCC TCC CTG CGT GCT CTG CGT CAG ATG TAATGATAG                     564
Ser Ser Leu Arg Ala Leu Arg Gln Met
            180                 185
```

Figure 1.

```
GCT CCG GTT CCG CCA GGA GAA GAT TCC AAA GAT GTA GCC GCC CCA CAC    048
Ala Pro Val Pro Pro Gly Glu Asp Ser Lys Asp Val Ala Ala Pro His
 1           5                   10                  15

AGA CAG CCG CTC ACC TCT TCA GAA CGA ATC GAT AAA CAA ATT CGG TAC    096
Arg Gln Pro Leu Thr Ser Ser Glu Arg Ile Asp Lys Gln Ile Arg Tyr
             20                  25                  30

ATC CTC GAC GGG ATA TCA GCG CTG AGA AAA GAG ACC AGC AAC AAG AGT    144
Ile Leu Asp Gly Ile Ser Ala Leu Arg Lys Glu Thr Ser Asn Lys Ser
         35                  40                  45

AAC ATG AGC GAA AGC AGT AAA GAA GCA CTG GCA GAA AAC AAC CTG AAC    192
Asn Met Ser Glu Ser Ser Lys Glu Ala Leu Ala Glu Asn Asn Leu Asn
     50                  55                  60

CTT CCG AAG ATG GCT GAA AAA GAT GGA TGT TTT CAA TCT GGA TTC AAT    240
Leu Pro Lys Met Ala Glu Lys Asp Gly Cys Phe Gln Ser Gly Phe Asn
 65                  70                  75                  80

GAG GAA ACT TGT CTG GTG AAA ATC ATC ACA GGC CTT TTG GAA TTT GAG    288
Glu Glu Thr Cys Leu Val Lys Ile Ile Thr Gly Leu Leu Glu Phe Glu
             85                  90                  95

GTA TAC CTA GAG TAC CTC CAG AAC AGA TTT GAG AGT AGT GAG GAA CAA    336
Val Tyr Leu Glu Tyr Leu Gln Asn Arg Phe Glu Ser Ser Glu Glu Gln
         100                 105                 110

GCG AGA GCT GTC CAG ATG TCG ACC AAA GTC CTG ATC CAG TTT CTG CAG    384
Ala Arg Ala Val Gln Met Ser Thr Lys Val Leu Ile Gln Phe Leu Gln
     115                 120                 125

AAA AAG GCA AAA AAT CTA GAT GCA ATA ACC ACC CCG GAT CCA ACC ACA    432
Lys Lys Ala Lys Asn Leu Asp Ala Ile Thr Thr Pro Asp Pro Thr Thr
 130                 135                 140

AAT GCG AGC CTG CTG ACG AAG CTG CAG GCA CAG AAC CAG TGG CTG CAG    480
Asn Ala Ser Leu Leu Thr Lys Leu Gln Ala Gln Asn Gln Trp Leu Gln
145                 150                 155                 160

GAC ATG ACA ACT CAT CTC ATT CTG AGA TCT TTC AAA GAA TTC CTG CAG    528
Asp Met Thr Thr His Leu Ile Leu Arg Ser Phe Lys Glu Phe Leu Gln
             165                 170                 175

TCC TCC CTG CGT GCT CTG CGT CAG ATG TAATGATAG                      564
Ser Ser Leu Arg Ala Leu Arg Gln Met
         180                 185
```

Figure 2.

| | | | | | | | | | | | | | | | | |
|---|---|---|---|---|---|---|---|---|---|---|---|---|---|---|---|---|
|CCA|GGA|GAA|GAT|TCC|AAA|GAT|GTA|GCC|GCC|CCA|CAC|AGA|CAG|CCG|CTC|048|
|Pro|Gly|Glu|Asp|Ser|Lys|Asp|Val|Ala|Ala|Pro|His|Arg|Gln|Pro|Leu| |
|1| | | |5| | | |10| | | | |15| | | |

| | | | | | | | | | | | | | | | | |
|---|---|---|---|---|---|---|---|---|---|---|---|---|---|---|---|---|
|ACC|TCT|TCA|GAA|CGA|ATC|GAT|AAA|CAA|ATT|CGG|TAC|ATC|CTC|GAC|GGG|096|
|Thr|Ser|Ser|Glu|Arg|Ile|Asp|Lys|Gln|Ile|Arg|Tyr|Ile|Leu|Asp|Gly| |
| | |20| | | | |25| | | | |30| | | | |

| | | | | | | | | | | | | | | | | |
|---|---|---|---|---|---|---|---|---|---|---|---|---|---|---|---|---|
|ATA|TCA|GCG|CTG|AGA|AAA|GAG|ACC|AGC|AAC|AAG|AGT|AAC|ATG|AGC|GAA|144|
|Ile|Ser|Ala|Leu|Arg|Lys|Glu|Thr|Ser|Asn|Lys|Ser|Asn|Met|Ser|Glu| |
| |35| | | | |40| | | | |45| | | | | |

| | | | | | | | | | | | | | | | | |
|---|---|---|---|---|---|---|---|---|---|---|---|---|---|---|---|---|
|AGC|AGT|AAA|GAA|GCA|CTG|GCA|GAA|AAC|AAC|CTG|AAC|CTT|CCG|AAG|ATG|192|
|Ser|Ser|Lys|Glu|Ala|Leu|Ala|Glu|Asn|Asn|Leu|Asn|Leu|Pro|Lys|Met| |
|50| | | | |55| | | | |60| | | | | | |

| | | | | | | | | | | | | | | | | |
|---|---|---|---|---|---|---|---|---|---|---|---|---|---|---|---|---|
|GCT|GAA|AAA|GAT|GGA|TCT|TTT|CAA|TCT|GGA|TTC|AAT|GAG|GAA|ACT|TCT|240|
|Ala|Glu|Lys|Asp|Gly|Ser|Phe|Gln|Ser|Gly|Phe|Asn|Glu|Glu|Thr|Ser| |
|65| | | | |70| | | | |75| | | | |80| |

| | | | | | | | | | | | | | | | | |
|---|---|---|---|---|---|---|---|---|---|---|---|---|---|---|---|---|
|CTG|GTG|AAA|ATC|ATC|ACA|GGC|CTT|TTG|GAA|TTT|GAG|GTA|TAC|CTA|GAG|288|
|Leu|Val|Lys|Ile|Ile|Thr|Gly|Leu|Leu|Glu|Phe|Glu|Val|Tyr|Leu|Glu| |
| | | | |85| | | | |90| | | | |95| | |

| | | | | | | | | | | | | | | | | |
|---|---|---|---|---|---|---|---|---|---|---|---|---|---|---|---|---|
|TAC|CTC|CAG|AAC|AGA|TTT|GAG|AGT|AGT|GAG|GAA|CAA|GCG|AGA|GCT|GTC|336|
|Tyr|Leu|Gln|Asn|Arg|Phe|Glu|Ser|Ser|Glu|Glu|Gln|Ala|Arg|Ala|Val| |
| | | |100| | | | |105| | | | |110| | | |

| | | | | | | | | | | | | | | | | |
|---|---|---|---|---|---|---|---|---|---|---|---|---|---|---|---|---|
|CAG|ATG|TCG|ACC|AAA|GTC|CTG|ATC|CAG|TTT|CTG|CAG|AAA|AAG|GCA|AAA|384|
|Gln|Met|Ser|Thr|Lys|Val|Leu|Ile|Gln|Phe|Leu|Gln|Lys|Lys|Ala|Lys| |
| | |115| | | | |120| | | | |125| | | | |

| | | | | | | | | | | | | | | | | |
|---|---|---|---|---|---|---|---|---|---|---|---|---|---|---|---|---|
|AAT|CTA|GAT|GCA|ATA|ACC|ACC|CCG|GAT|CCA|ACC|ACA|AAT|GCG|AGC|CTG|432|
|Asn|Leu|Asp|Ala|Ile|Thr|Thr|Pro|Asp|Pro|Thr|Thr|Asn|Ala|Ser|Leu| |
| |130| | | | |135| | | | |140| | | | | |

| | | | | | | | | | | | | | | | | |
|---|---|---|---|---|---|---|---|---|---|---|---|---|---|---|---|---|
|CTG|ACG|AAG|CTG|CAG|GCA|CAG|AAC|CAG|TGG|CTG|CAG|GAC|ATG|ACA|ACT|480|
|Leu|Thr|Lys|Leu|Gln|Ala|Gln|Asn|Gln|Trp|Leu|Gln|Asp|Met|Thr|Thr| |
|145| | | | |150| | | | |155| | | | |160| |

| | | | | | | | | | | | | | | | | |
|---|---|---|---|---|---|---|---|---|---|---|---|---|---|---|---|---|
|CAT|CTC|ATT|CTG|AGA|TCT|TTC|AAA|GAA|TTC|CTG|CAG|TCC|TCC|CTG|CGT|528|
|His|Leu|Ile|Leu|Arg|Ser|Phe|Lys|Glu|Phe|Leu|Gln|Ser|Ser|Leu|Arg| |
| | | | |165| | | | |170| | | | |175| | |

| | | | | | | |
|---|---|---|---|---|---|---|
|GCT|CTG|CGT|CAG|ATG|TAATGATAGG TACCGAGCTC GAATTCGTCG ACCTGCAGCC|583|
|Ala|Leu|Arg|Gln|Met| | |
| | | | |180| | |

AAGCTT                                                                      589 pBgal/EK/cfIL-6

Figure 6.

| | |
|---|---|
| CC ATG GCT CCG GTT CCG CCA GGA GAA GAT TCC AAA GAT GTA GCC GCC<br>   Met Ala Pro Val Pro Pro Gly Glu Asp Ser Lys Asp Val Ala Ala<br>    1                 5                10                15 | 047 |
| CCA CAC AGA CAG CCG CTC ACC TCT TCA GAA CGA ATC GAT AAA CAA ATT<br>Pro His Arg Gln Pro Leu Thr Ser Ser Glu Arg Ile Asp Lys Gln Ile<br>                20                      25                 30 | 095 |
| CGG TAC ATC CTC GAC GGG ATA TCA GCG CTG AGA AAA GAG ACC AGC AAC<br>Arg Tyr Ile Leu Asp Gly Ile Ser Ala Leu Arg Lys Glu Thr Ser Asn<br>            35                     40                    45 | 143 |
| AAG AGT AAC ATG AGC GAA AGC AGT AAA GAA GCA CTG GCA GAA AAC AAC<br>Lys Ser Asn Met Ser Glu Ser Ser Lys Glu Ala Leu Ala Glu Asn Asn<br>     50                    55                    60 | 191 |
| CTG AAC CTT CCG AAG ATG GCT GAA AAA GAT GGA TGT TTT CAA TCT GGA<br>Leu Asn Leu Pro Lys Met Ala Glu Lys Asp Gly Cys Phe Gln Ser Gly<br>    65                   70                    75 | 239 |
| TTC AAT GAG GAA ACT TGT CTG GTG AAA ATC ATC ACA GGC CTT TTG GAA<br>Phe Asn Glu Glu Thr Cys Leu Val Lys Ile Ile Thr Gly Leu Leu Glu<br> 80                85                  90                95 | 287 |
| TTT GAG GTA TAC CTA GAG ATA CCT CCG AAC AGA TTT GAG AGT AGT GAG<br>Phe Glu Val Tyr Leu Glu Ile Pro Pro Asn Arg Phe Glu Ser Ser Glu<br>          100                 105               110 | 335 |
| GAA CAA GCG AGA GCT GTC CAG ATG TCG ACC AAA GTC CTG ATC CAG TTT<br>Glu Gln Ala Arg Ala Val Gln Met Ser Thr Lys Val Leu Ile Gln Phe<br>        115                 120               125 | 383 |
| CTG CAG AAA AAG GCA AAA AAT CTA GAT GCA ATA ACC ACC CCG GAT CCA<br>Leu Gln Lys Lys Ala Lys Asn Leu Asp Ala Ile Thr Thr Pro Asp Pro<br>        130                 135               140 | 431 |
| ACC ACA AAT GCG AGC CTG CTG ACG AAG CTG CAG GCA CAG AAC CAG TGG<br>Thr Thr Asn Ala Ser Leu Leu Thr Lys Leu Gln Ala Gln Asn Gln Trp<br>    145                   150               155 | 479 |
| CTG CAG GAC ATG ACA ACT CAT CTC ATT CTG AGA TCT TTC AAA GAA TTC<br>Leu Gln Asp Met Thr Thr His Leu Ile Leu Arg Ser Phe Lys Glu Phe<br>160                 165               170               175 | 527 |
| CTG CAG TCC TCC CTG CGT GCT CTG CTT CAG ATG TAATGATAGG TACCGAGCTC<br>Leu Gln Ser Ser Leu Arg Ala Leu Leu Gln Met<br>              180                 185 | 580 |
| GAATTCGTCG ACCTGCAGCC AAGCTT | 606 |

Figure 12.

```
AAG CTT GAT CAG GCG GAT CCG GAA GGT GGT AGC GAC GAC GAC GAC AAA    048
Lys Leu Asp Gln Ala Asp Pro Glu Gly Gly Ser Asp Asp Asp Asp Lys
-16 -15              -10                  -5

CCG GTT CCG CCA GGA GAA GAT TCC AAA GAT GTA GCC GCC CCA CAC AGA    096
Pro Val Pro Pro Gly Glu Asp Ser Lys Asp Val Ala Ala Pro His Arg
 1               5                  10                  15

CAG CCG CTC ACC TCT TCA GAA CGA ATC GAT AAA CAA ATT CGG TAC ATC    144
Gln Pro Leu Thr Ser Ser Glu Arg Ile Asp Lys Gln Ile Arg Tyr Ile
            20                  25                  30

CTC GAC GGG ATA TCA GCG CTG AGA AAA GAG ACC AGC AAC AAG AGT AAC    192
Leu Asp Gly Ile Ser Ala Leu Arg Lys Glu Thr Ser Asn Lys Ser Asn
        35                  40                  45

ATG AGC GAA AGC AGT AAA GAA GCA CTG GCA GAA AAC AAC CTG AAC CTT    240
Met Ser Glu Ser Ser Lys Glu Ala Leu Ala Glu Asn Asn Leu Asn Leu
    50                  55                  60

CCG AAG ATG CGT GAA AAA GAT GGA TCT TTT CAA TCT GGA TTC AAT GAG    288
Pro Lys Met Arg Glu Lys Asp Gly Ser Phe Gln Ser Gly Phe Asn Glu
65                  70                  75                  80

GAA ACT TCT CTG GTG AAA ATC ATC ACA GGC CTT TTG GAA TTT GAG GTA    336
Glu Thr Ser Leu Val Lys Ile Ile Thr Gly Leu Leu Glu Phe Glu Val
                85                  90                  95

TAC CTA GAG TAC CTC CAG AAC AGA TTT GAG AGT AGT GAG GAA CAA GCG    384
Tyr Leu Glu Tyr Leu Gln Asn Arg Phe Glu Ser Ser Glu Glu Gln Ala
            100                 105                 110

AGA GCT GTC CAG ATG TCG ACC AAA GTC CTG ATC CAG TTT CTG CAG AAA    432
Arg Ala Val Gln Met Ser Thr Lys Val Leu Ile Gln Phe Leu Gln Lys
        115                 120                 125

AAG GCA AAA AAT CTA GAT GCA ATA ACC ACC CCG GAT CCA ACC ACA AAT    480
Lys Ala Lys Asn Leu Asp Ala Ile Thr Thr Pro Asp Pro Thr Thr Asn
    130                 135                 140

GCG AGC CTG CTG ACG AAG CTG CAG GCA CAG AAC CAG TGG CTG CAG GAC    528
Ala Ser Leu Leu Thr Lys Leu Gln Ala Gln Asn Gln Trp Leu Gln Asp
145                 150                 155                 160

ATG ACA ACT CAT CTC ATT CTG AGA TCT TTC AAA GAA TTC CTG CAG TCC    576
Met Thr Thr His Leu Ile Leu Arg Ser Phe Lys Glu Phe Leu Gln Ser
                165                 170                 175

TCC CTG CGT GCT CTG CGT CAG ATG TAATGATAG GTACC                    614
Ser Leu Arg Ala Leu Arg Gln Met           Val
            180                           185
```

CYSTEINE DEPLETED IL-6 MUTEINS

This application is a continuation-in-part of Ser. No. 07/724,698 filed Jul. 2, 1991, now incorporated herein by reference.

FIELD OF THE INVENTION

The present invention is directed to muteins of IL-6. More specifically, the invention is directed to full-length and truncated muteins of IL-6 wherein the cysteine residues corresponding to amino acid positions 45 and 51 of native IL-6 have been replaced by other amino acids, while the cysteine residues corresponding to amino acid positions 74 and 84 have been retained.

BACKGROUND OF THE INVENTION

Interleukin-6 (IL-6) is a term given to a protein described by numerous synonyms in the literature. Some examples include interferon-beta-2 (IFN-B2), B-cell stimulation factor-2 (BSF-2), B-cell hybridoma/plasmacytoma growth factor (HPGF or HGF), 26 kDa protein and hepatocyte stimulating factor (HSF); see interferon-beta-2 (Zilberstein et al., EMBO J. 5, 2519 (1986)); 26 kDa protein (Haegeman et al., Eur. J. Biochem. 159, 625 (1986)); B-cell stimulation factor-2 (Hirano et al., Nature 324, 73 (1986)); B-cell hybridoma/plasmacytoma growth factor (Van Snick et al., Proc. Natl. Acad. Sci. 83, 9679 (1986)); Billiau, Immunol. Today 8, 84 (1987)); Van Damme et al., Eur. J. Biochem. 168, 543 (1987)); Tosato et al., Science 239, 502 (1988); and hepatocyte stimulating factor (Gauldie et al., Proc. Natl. Acad. Sci. 84, 7251 (1987)).

The sequence of hybridoma growth factor, and, therefore, of IL-6, is given by Brakenhoff et al, Journal of Immunology 139, 4116–4121 (1987); see FIG. 2A on page 4119. The amino acid sequence consists of a signal peptide followed by the mature, full-length HGF protein.

There is controversy regarding the position at which the signal peptide ends and the mature protein begins. The signal peptide is described as ending with the 27th amino acid (proline) or the 28th amino acid (alanine). The mature full-length protein contains the 185 amino acid residues starting with alanine or the 184 amino acid residues starting with proline. Different sources produce different mixtures of full length and truncated forms of IL-6, including full length IL-6, IL-6 lacking the first two amino acids, i.e. AlaPro and/or IL-6 lacking the first amino acid, i.e. Ala. See Van Damme, "Biochemical and Biological Properties of Human HPGF/IL-6" in Interleukin-6, Sehgal et al., eds., (Volume 557 of the New York Academy of Sciences), Page 104–109 at 107 (1989).

FIG. 2C in the Brakenhoff et al. article describes the differences in the nucleotide sequences that code for HGF, IFN-beta-2, 26 kd protein and BSF-2. These differences consist of a T at nucleotide 46 in 26 kd protein and a C corresponding to this position in the other three sequences; and a C at position 429 in IFN beta-2 and a G corresponding to this in this position in the other three sequences; see page 4118, column 1, the second full paragraph of Brakenhoff et al., Journal of Immunology 139, 4116–4121 (1987). Both differences are described by Brakenhoff et al. as silent point mutations. Therefore, the amino acid sequence of HGF, IFN-beta-2, 26kd protein and BSF-2 are considered to be different names for the same protein. For the purposes of the present invention, the amino acid sequence of mature, native, full-length IL-6 is considered to be the same as that of HGF, IFN-beta-2, 26kd protein, and BSF-2.

IL-6 has been reported to be an important cytokine with numerous significant biological activities. The activities of IL-6 often occur in conjunction with other growth factors, such as other interleukins and TNF. Thus, IL-6 is believed to play an important role in the regulation of inflammatory and immune responses to infection and injury. For example, IL-6 has been demonstrated to be involved in the proliferation and differentiation of B cells, T cells and multi-potential hematopoietic progenitor cells.

In addition, IL-6 has been observed to be involved in the inflammatory response and to induce various acute phase proteins in liver cells. Additional evidence of the involvement of IL-6 in the inflammatory response is the presence of high concentrations of IL-6 in the bodily fluids of patients with severe burns, kidney transplants, acute infections of the central nervous system, rheumatoid arthritis, and septic shock.

IL-6 has also been shown to stimulate megakaryocytopoiesis and platelet production. See McDonald et al., Blood 77, 735–740 (1991) and Hill et al., Blood 77, 42–48 (1991).

The biological activities of IL-6 suggest important immuno-therapeutic and anti-inflammation compositions. Immuno-therapeutic compositions containing IL-6 and other interleukins have, for example, been suggested by Kishimoto et al. (Ajinomoto Company, Inc.), European patent application 257,406.

Small amounts of human IL-6 may be isolated from natural sources, such as cells that secret IL-6. A number of cells secrete IL-6, including monocytes, T cells, fibroblasts, keratinocytes, and endothelial cells.

With the advent of recombinant DNA techniques, it has been found possible to produce larger amounts of pure IL-6 by expression in suitable host cells, such as *E. coli*, injected Xenopus oocytes, cell-free reticulocyte lysate, insect cells, and mammalian cells. For example, expression in Xenopus oocytes and cell-free reticulocyte lysate has been described by Revel et al. in UK patent application 2,063,882. Expression in *E. coli* has been reported by Snouwaert in the Journal of Immunology 146, 583–591 (1991); Brakenhoff et al. in the Journal of Immunology 145, 561–568 (1990), the Journal of Immunology 143, 1175–1182 (1989), and the Journal of Immunology 139, 4116–4121 (1987); Asagoe in Biotechnology 6, 806–809 (1988); and Yasueda in Biotechnology 8, 1036–1040 (1990).

Commercially, it is desirable to be able to produce proteins in *E. coli*. The ability to express large amounts of IL-6 in *E. coli*, however, has been reported to be associated with certain problems that need to be overcome. For example, Asagoe et al. were unsuccessful in expressing IL-6 in *E. coli* until they prepared an HGF fusion protein with a factor Xa-specific cleavage sequence; see Biotechnology 6, 806–809 (1988). Similarly, Yasueda et al. had to introduce dual Shine-Delgarno sequences in front of the coding region and employed A-T rich sequences between the Shine-Delgarno region and the initiation codon as well as in the codons for the N-terminal region of the protein in order to achieve high expression levels; see Biotechnology 8, 1036–1040 (1990).

In addition to being able to prepare large amounts of pure protein, recombinant DNA techniques permit molecular biologists to improve on the proteins that occur in nature. For example, it is possible to prepare proteins that lack some of the amino acids present in the native protein. Thus, Brakenhoff et al. has reported that the biological activity of IL-6 is not affected by deletion of up to 28 amino acid residues from the mature, native IL-6; see the Journal of Immunology 143, 1175–1182 (1989).

Native proteins may also be improved by substituting amino acids for one or more of the amino acids that occur naturally in a protein. Such substitutions may be introduced into a protein by expressing recombinant DNA having a nucleotide sequence modified so as to have a codon that represents the desired amino acid. The DNA may conveniently be modified using the technique of directed mutagenesis. Proteins expressed by such modified DNA are called muteins. Directed mutagenesis techniques have been reviewed by Lather et al. in Genetic Engineering, Academic Press, pages 31–50 (1983) and by Smith and Gillam in Genetic Engineering; Principles and Methods, Plenum Press, Volume 3, pages 1–32 (1981).

There have, for example, been recommendations to substitute cysteine residues in native interferon beta with other amino acids; see Mark et al., U.S. Pat. No. 4,853,332. The cysteine residues in interferon beta reportedly form undesirable inter-molecular and intramolecular bonds that affect activity and the ease with which the protein can be expressed in *E. coli*. Mark et al. speculate that the method may usefully be applied ". . . to any other biologically active protein that contains a functionally non-essential cysteine residue that makes the protein susceptible to undesirable disulfide bond formation."

Mark et al. recognized, of course, that one cannot always replace a cysteine residue and still retain biological activity. If the cysteine residue forms a disulfide bond that is essential to the tertiary structure of the protein, replacement of the cysteine will cause at least some loss of biological activity. According to Mark et al., the literature may be consulted for ". . . information regarding the cysteine content of biologically active proteins and the roles played by the cysteine residues with respect to activity and tertiary structure."

Recommendations have been made to replace one or more of the cysteine residues in IL-6; see Clark et al., PCT application WO88/00206. Several pieces of evidence, however, suggest that doing so is undesirable.

For example, one guideline suggested by Mark et al. in U.S. Pat. No. 4,853,332 for predicting which proteins are susceptible to having cysteine residues replaced by other amino acids is that such proteins usually have an odd number of cysteine residues. There are four cysteine residues in IL-6. Therefore, IL-6 is inconsistent with a guideline proposed by Mark et al.

In addition, Snouwaert et al., in the Journal of Immunology 146, 585–591 (1991), disclose that the replacement of the four cysteine residues in IL-6 resulted in significant loss of activity in four in vitro cell proliferation assays, especially when human cells were employed in the assays. This did not surprise Snouwaert et al., who noted that IL-6 and G-CSF are known to have significant homology, and that the disulfide structures of human IL-6 and human G-CSF are known to be similar; see Clogston et al., Archives of Biochemistry and Biophysics 272, 144–151 (1989). Since it is also known that substitution of any one of the four conserved cysteine residues in human G-CSF results in loss of biological activity, Snouwaert et al. reason that the loss of activity in cysteine-free IL-6 was expected.

Snouwaert et al. also conducted experiments to determine which regions of the IL-6 molecule are necessary for activity. They prepared a series of IL-6 mutants in which segments of twenty amino acids each were missing throughout the length of native IL-6. Only the mutant from which amino acid residues 4–23 were deleted retained significant activity. Each of the other deletions abolished activity. Snouwaert et al. conclude that disulfide bonding is important in maintaining the biologically active conformation of human IL-6.

Additional evidence for the importance of the cysteine residues for activity of IL-6 may be found in an article by Brakenhoff et al. in the Journal of Immunology 145, 561–568 (1990). Brakenhoff et al. used epitope mapping of specific monoclonal antibodies to study the active sites of IL-6. They conclude that there is an active site on the IL-6 molecule between amino acid residues 29 (glutamine) and 34 (leucine). This region is only 11 amino acids residues from the first cysteine residue at position 45. The proximity of the active site to this cysteine residue suggests that at least the first disulfide bond, and, therefore, the first two cysteine residues at positions 45 and 51, are necessary for activity. Brakenhoff et al. express the opinion that a second active site exists on IL-6, although the location of the second active site is uncertain.

Muteins and truncated versions of IL-6 are desirable. It is especially desirable, and the principal objective of the present invention, to produce cysteine-depleted muteins having at least comparable activity to that of native IL-6 despite evidence that such muteins do not exist.

SUMMARY OF THE INVENTION

These and other objectives, as will become apparent to those with skill in the art, have been met by providing a mutein of IL-6 wherein the cysteine residues at positions 45 and 51 of native IL-6 have each been replaced by other amino acids, and the cysteine residues at positions 74 and 84 have been retained.

BRIEF DESCRIPTION OF THE FIGURES

FIG. 1 shows the amino acid sequence of a full length mutein of human IL-6 starting with alanine (IL-6 SSCC) (SEQ ID NO: 1 and SEQ ID NO: 2). The cysteine residues at positions 45 and 51 of native IL-6 have been replaced by serine residues. The cysteine residues at positions 74 and 84 of native IL-6 have been retained. The nucleotide sequence used to express the IL-6 mutein is also shown.

FIG. 2 shows the 0.580 kb Eco RII/HindIII IL-6 fragment described in Example 2 as Sequence A.

FIG. 6 shows the NcoI/HindIII fragment of pKK IL-6 SSCC (SEQ ID NO: 5 and SEQ ID NO: 6). See Example 5.

FIG. 7 shows a chromatogram of the elution of the -22aa IL-6 SSCC fraction following elution from a Phenyl-sepharose hydrophobic interaction column. The absorbance of the fractions at 280 nm versus time in minutes and the gradient profile of conductivity is compared; see Example 10a.

FIG. 12 shows the HindIII/KpnI IL-6 containing fragment of pTrpE/EK/cfIL-6; see Example 13.

DETAILED DESCRIPTION OF THE INVENTION

Definitions

Figure 3:
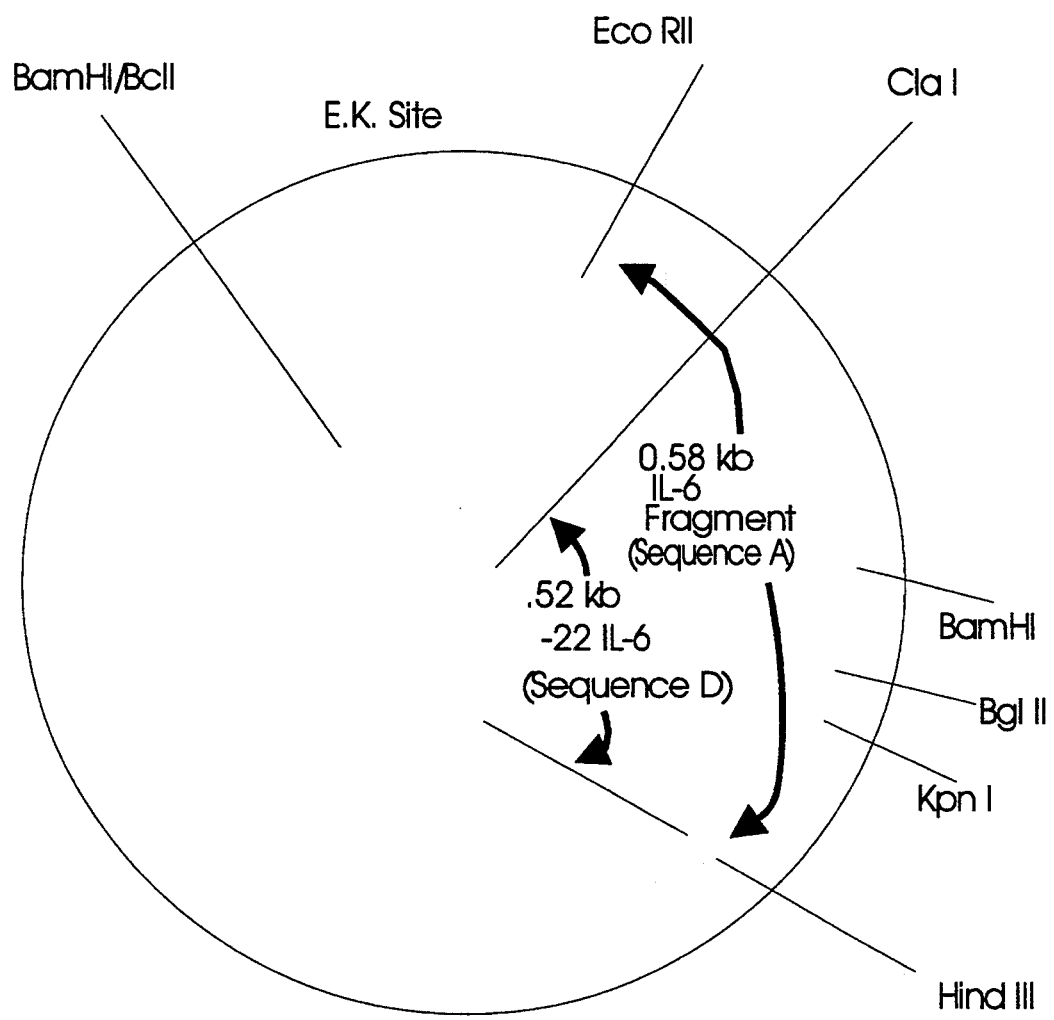
FIG. 3 shows the plasmid described in Example 1 as pBeta gal/EK/cfIL-6 (SEQ ID NO: 7 and SEQ ID NO: 8).

The present invention is directed to muteins of IL-6 having biological activity at least comparable to that of native IL-6. In this specification, IL-6 refers to human IL-6, and includes proteins described in the literature as having the same name as IL-6. Such proteins include interferon-beta-2 (IFN-B2), B-cell stimulation factor-2 (BSF-2), B-cell hybridoma/plasmacytoma growth factor (HPGF or HGF), 26 kDa protein, and hepatocyte stimulating factor (HSF).

The amino acid sequence of IL-6 has been described in the literature; see, for example, FIG. 2A of Brakenhoff et al., Journal of Immunology 139, 4116–4121 (1987) and FIG. 1 of Clark et al., PCT application WO 88/00206. These references also contain the cDNA sequence that corresponds to native IL-6 mRNA.

Native IL-6 contains four cysteine residues, which occur at positions 45, 51, 74 and 84 of the mature, full length sequence. These positions are based on the definition in this specification that the mature, native, full length IL-6 contains 185 amino acids starting with alanine as residue 1. The words "amino acid" in this specification are understood to mean the 20 naturally occurring alpha-amino acids. In the muteins of the invention, the cysteine residues that correspond to positions 45 and 51 of native IL-6 have each been replaced by any other amino acid. The cysteine residues that correspond to positions 74 and 84 of native IL-6 are retained in the muteins of the invention.

The inventors have made an unexpected discovery. One would have predicted that the activity of IL-6 would have been most affected by replacing the first two cysteine residues with other amino acids. It will be remembered that these cysteine residues were predicted by Brakenhoff et al. to form a disulfide bond in the proximity of an active site (see above).

Therefore, the inventors first attempted to replace the third and fourth cysteine residues with other residues. The first residue tried was serine.

When the third and fourth cysteine residues were replaced by serine residues, however, the resulting mutein had relatively little activity. The third and fourth cysteine residues, which occur at positions 74 and 84 of mature, native, full length IL-6, were predicted by Brakenhoff et al. to be farther from the active site than the first two cysteine residues.

The inventors were, therefore, surprised to find that when they replaced the first two cysteine residues with serine residues, the resulting mutein has good activity, i.e. at least comparable to that of native IL-6. Replacement of the first two cysteine residues with residues other than serine also results in IL-6 muteins with good activity.

FIG. 1 shows the amino acid sequence of one example of a cysteine-depleted IL-6 mutein of the invention, This sequence is identical to that of native IL-6, except for the replacement of the natural cysteine residues at positions 45 and 51 with serine residues. A nucleotide sequence that expresses the mutein is also shown in FIG. 1.

In this specification, a mutein of IL-6 that contains cysteine residues at positions 74 and 84, but not at positions 45 and 51, is called IL-6 XXCC wherein X represents any naturally occurring alpha amino acid or an amino acid analogue. Preferably, X represents a neutral amino acid. The preferred neutral amino acids include alanine, serine, threonine, proline and glycine. More preferred amino acids for replacing the cysteine residues are serine and alanine.

The two amino acids that replace the cysteine residues at positions corresponding to 45 and 51 of native, mature IL-6 (XX) may be the same or different. Some examples of XX include SS, AA, GG, DR, RD, SA, AS, etc.

Thus, the amino acid sequence shown in FIG. 1 is referred to herein as IL-6 SSCC. Where there is no indication of which cysteine residues have been replaced, and which amino acids have replaced them, it will be assumed that the first and second cysteine residues have been replaced by serine residues, as in IL-6 SSCC.

The mutein of the invention may contain all 185 amino acid residues corresponding to full length native IL-6, as shown in FIG. 1. Alternatively, from 1 to 28 N-terminal amino acid residues may be deleted. A deleted form of the muteins of the invention will be designated -naa IL-6 cys XXCC, wherein X is as defined above, and n represents the number of missing amino acid residues. Thus, a truncated mutein lacking the N-terminal 22 amino acids is designated -22aa IL-6 cys XXCC.

The alanine at position 1 and the alanine-proline at positions 1 and 2 of mature, full length IL-6 are sometimes cleaved during processing of the protein. Therefore, the muteins of the invention often comprise pure IL-6 cys XXCC, pure -1aa IL-6 cys XXCC, pure -2aa IL-6 cys XXCC or a mixture of two or three of IL-6 cys XXCC, -1aa IL-6 cys XXCC and -2aa IL-6 cys XXCC.

The position of an amino acid in the sequence of a truncated mutein is defined as corresponding to a position of an amino acid in native IL-6 as if the mutein were full length. For example, if a serine residue replaces a cysteine residue at position 45 of full length IL-6, and the N-terminal 22 amino acids are removed, the first amino acid of the truncated form, serine, would correspond to the 23rd amino acid residue of full length IL-6. The 23rd amino acid of the truncated mutein would correspond to the cysteine residue that is replaced at position 45 of full length IL-6.

The invention also includes nucleic acid molecules encoding the full length and truncated muteins of the invention. The nucleic acid molecules may be RNA or DNA. The DNA may be derived from natural sources, such as from genomic DNA or cDNA. The DNA may also be synthesized from the individual nucleotides.

The sequence of the nucleic acid molecule may be any sequence that encodes the corresponding mutein. The nucleic acid molecule may, for example, have the sequence of a native IL-6 gene. Preferably, the nucleic acid molecule will have a sequence that maximizes expression in the particular host cell used to express the IL-6 mutein.

The invention also includes equivalent variants of the muteins described above and the nucleic acid molecules that encode such variants. Equivalent variants include proteins comprising substitutions and additions in the amino acid and nucleotide sequences of the muteins of the invention and the corresponding nucleic acid molecules. Variants are included in the invention as long as the resulting muteins and nucleic acid molecules continue to satisfy the structural and functional criteria described above, i.e., retain activity at least comparable to that of native IL-6. An amino acid or nucleotide sequence that is substantially the same as another sequence, but that differs from the other sequence by means of one or more substitutions or additions is considered to be an equivalent sequence. Except for the substitutions of cysteine residues at positions corresponding to positions 45 and 51 of native, mature IL-6, preferably less than 25%, more preferably less than 10%, and most preferably less than 5% of the total number of amino acids or nucleotides in the muteins of the invention are substituted for or added to in the equivalent sequences.

For example, it is known to substitute amino acids in a sequence with equivalent amino acids. Groups of amino acids considered normally to be equivalent are:

(a) Ala(A) Ser(S) Thr(T) Pro(P) Gly(G);

(b) Asn(N) Asp(D) Glu(E) Gln(Q);

(c) His(H) Arg(R) Lys(K);

(d) Met(M) Leu(L) Ile(I) Val(V); and (e) Phe(F) Tyr(Y) Trp(W).

Additions to the full-length and truncated IL-6 muteins may be made at the C-terminal or N-terminal ends by adding the corresponding codons at the 5' or 3' ends of the nucleic acid sequences and expressing the nucleic acid molecules. Examples of internal additions to the nucleic acid molecules include the introns present in genomic DNA. The introns are not expressed in a suitable eukaryotic host cell.

Preparation of muteins

The muteins of the invention are preferably made by preparing and amplifying a corresponding nucleic acid molecule and expressing the mutein in a suitable host cell. Some examples of suitable host cells include bacterial, yeast, insect, and mammalian cells. The preferred host cell is a bacterial cell. *E. coli* is especially preferred.

DNA encoding the IL-6 muteins of the invention may be prepared by synthesis from the four individual nucleotides or by mutagenesis of a native IL-6 sequence or a variant of a native IL-6 sequence. Native IL-6 DNA may be isolated from a human cDNA or genomic DNA library. Native or mutated IL-6 DNA may also be isolated from a recombinant vector containing an IL-6 or variant IL-6 sequence. These methods are further described below.

Chemical synthesis of the DNA from the four nucleotides may be accomplished in whole or in part by methods known in the art. Such methods include those described by Caruthers in Science 230, 281-285 (1985). DNA may also be synthesized by preparing overlapping double-stranded oligonucleotides, filling in the gaps, and ligating the ends together. The synthesis of a DNA molecule encoding IL-6 from individual nucleotides by such methods is described by Yasueda et al. in Biotechnology 8, 1036-1040 (1990).

The coding region of the IL-6 gene or fragments of the gene may also be isolated from human cells by using the known DNA sequence to synthesize one or more suitable oligonucleotide probes. To do so, labelled oligonucleotides having a sequence complementary to that of a portion of one of the strands of IL-6 is prepared. A library of human cDNA or genomic DNA or a source of mRNA is then screened with the labelled probe or probes.

The preferred method for obtaining DNA suitable as a starting material for conversion to DNA encoding muteins of the invention is to isolate DNA encoding native IL-6 or a variant of native IL-6 from an available recombinant plasmid. Recombinant plasmids that encode native full length and truncated IL-6 containing the four cysteine residues are known; see, for example, Clark et al., PCT application WO88/00206; Brakenhoff et al., Journal of Immunology 143, 1175-1182 (1989); Brakenhoff et al., Journal of Immunology 139, 4116-4121 (1987); Hirano et al., Proc. Natl. Acad. Sci. USA 84, 228-231 (1987). The codons for the cysteine residues at positions corresponding to positions 45 and 51 of native IL-6 are replaced by codons for other amino acids, preferably by codons for other neutral amino acids, and more preferably by codons for serine or alanine residues. Replacement of the cysteines may be achieved by site-directed mutagenesis.

Alternatively, plasmids containing DNA that encodes variants of native IL-6 in which all four cysteine residues have been replaced by serine residues may be obtained as described in Fowlkes et al., U.S. patent application No. 89/05421. The codons for the serine residues at positions corresponding to positions 74 and 84 of native IL-6 are replaced by cysteine residues by, for example, site-directed mutagenesis. The codons for the serine residues at positions corresponding to 45 and 51 may be retained or replaced by other amino acid residues, such as by alanine, in the same way (see below). Site-directed mutagenesis is carried out by methods known in the art. See, for example, Zoller and Smith, Nucl. Acids Res. 10, 6487-6500 (1982); Methods in Enzymology 100, 468-500 (1983); and DNA 3, 479-488 (1984).

Since DNA encoding IL-6 containing all four cysteine residues and variants wherein all four cysteine residues have been replaced by other amino acid residues are known (Snouwaert et al, Journal of Immunology 146, 585-591 (1991)), the replacement of two cysteine residues may also be accomplished by a modification of the recombinant circle polymerase chain reaction (PCR) method described by Jones et al. in Biotechniques 8, 178-183 (1990).

Figure 13:
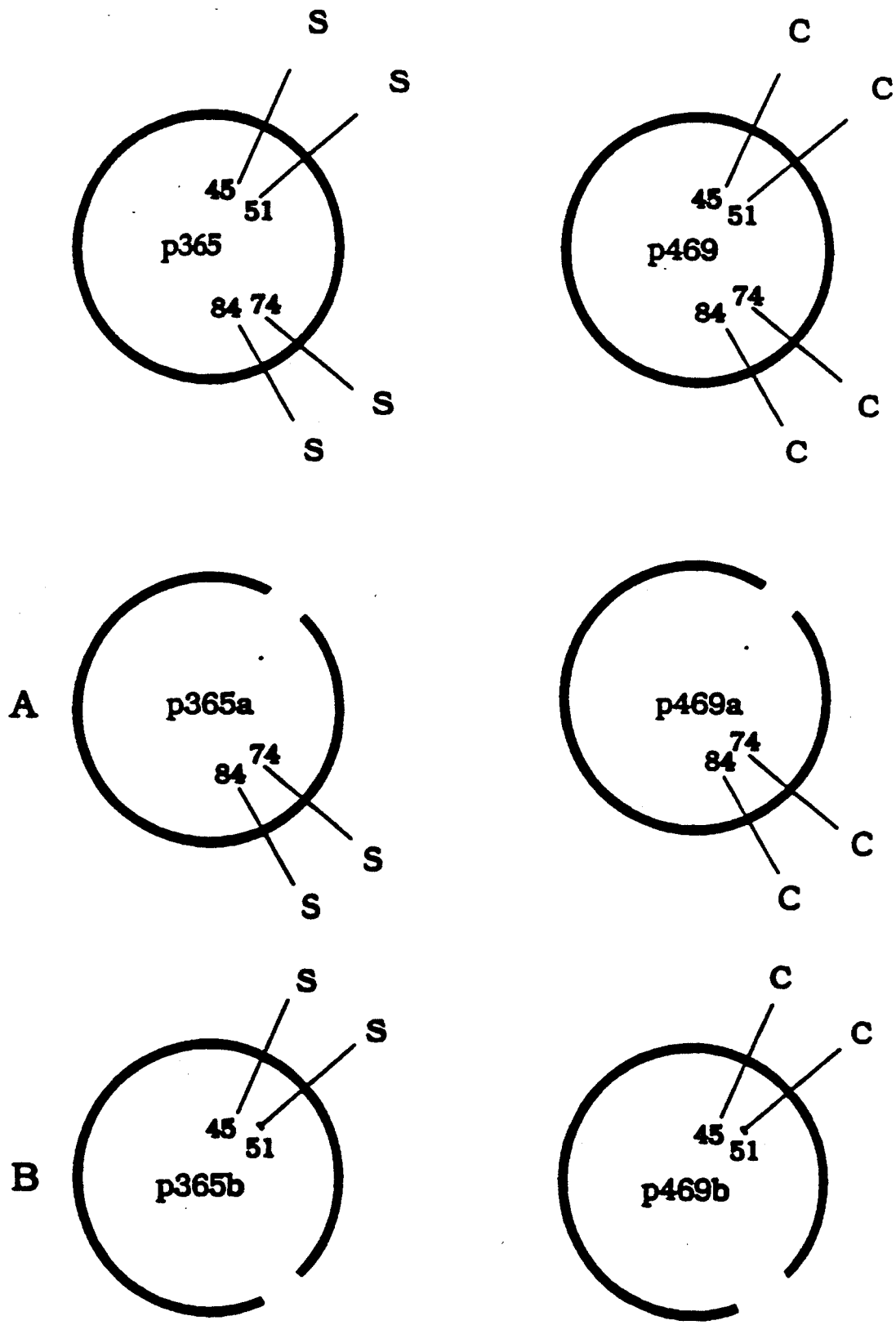
FIG. 13 shows the strategy described in Example 14B for preparing MetGly -2aa IL-6 SSCC and -CCSS by recombinant circle PCR.
Figure 14A:
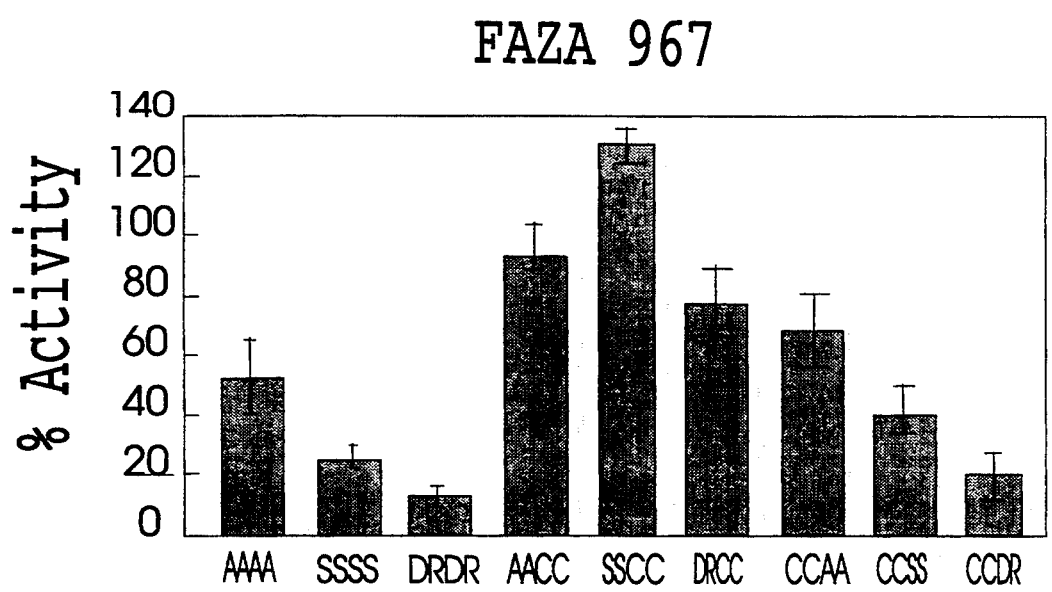
FIG. 14A–14D shows the biological activity of IL-6 mutant variants; see Example 15.
Figure 14B:
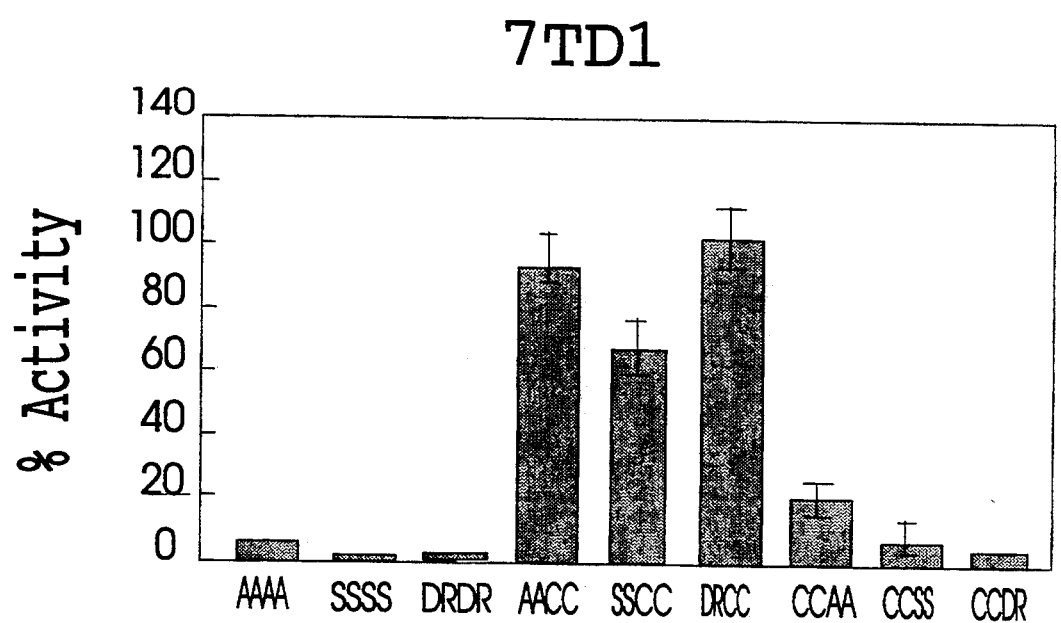
Figure 14C:
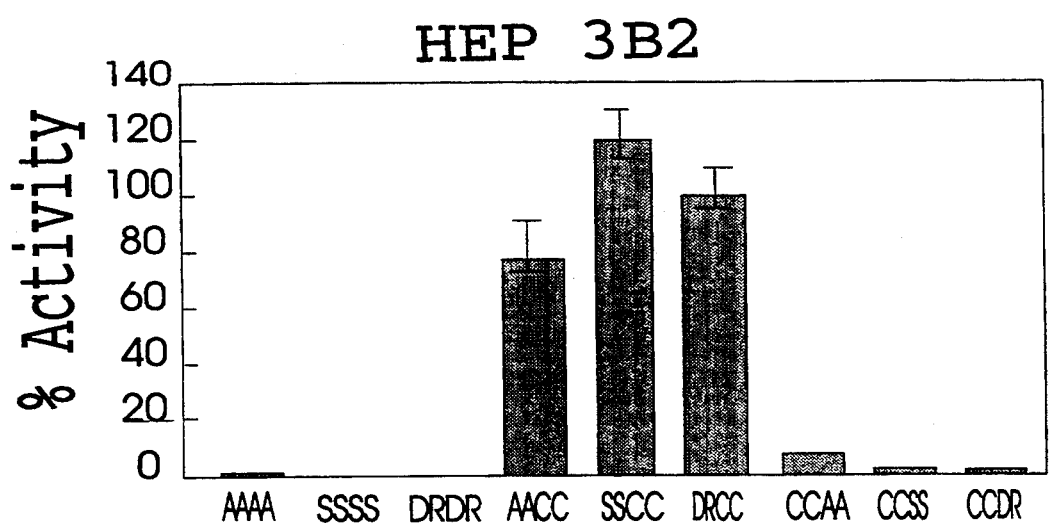
Figure 14D:
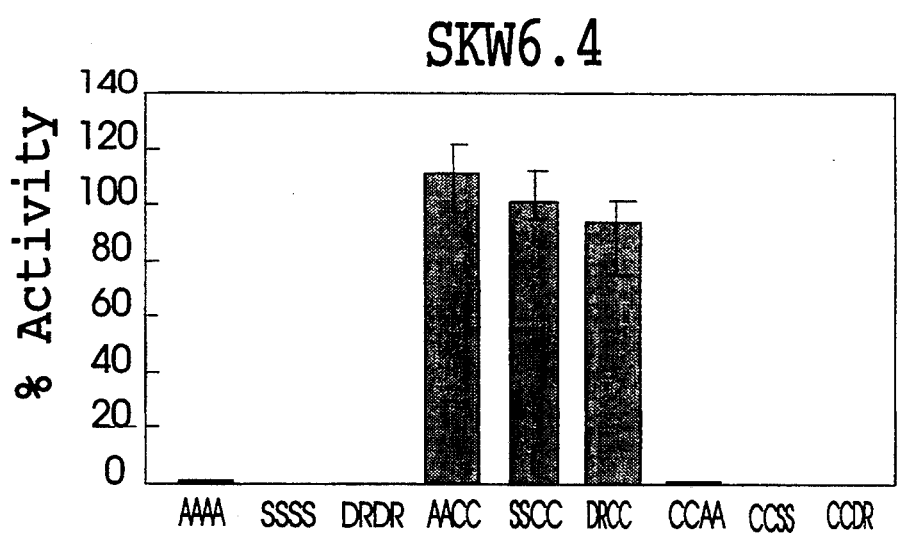

An example of the strategy is illustrated in FIG. 13. Two plasmids are used. One plasmid contains DNA encoding a cysteine-free variant of IL-6 wherein the cysteine residues are replaced by other residues. The other plasmid contains the corresponding DNA encoding cysteine-containing IL-6.

Each plasmid is amplified with two separate PCR primer sets. One primer set, designated a, is used to amplify the entire length of each plasmid with the exception of a region encoding the nucleotides corresponding to codons 45–51 of the native IL-6 sequence. The products of this type of reaction are designated as "a-(cys)" or "a-(cys-free)," depending on the template used in the reaction. In a similar manner, the same plasmids are used as templates in a second type of reaction using primer set b to produce products "b-(cys)" or "b-(cys-free)." These products include the entire sequence of each plasmid with the exception of the region encoding the nucleotides corresponding to codons 74–84 of the native IL-6 sequence.

After gel purification, products "a-(cys-free)" and "b-(cys)" are combined, denatured, and annealed to produce recombinant circles with two single stranded gaps. The single-stranded DNA across the first gap encodes amino acids other than cysteine residues at positions 45 and 51, while the single-stranded DNA across the second gap encodes cysteine residues at positions 74 and 84. After transformation into E. coli, these gapped circles are repaired to produce plasmids that carry a gene encoding an IL-6 mutein in which the cysteines at positions 45 and 51 are replaced by other amino acids. Further experimental details are provided in Example 14B.

Amplifying DNA

The DNA encoding the muteins of the invention may be amplified by methods known in the art. One suitable method is the polymerase chain reaction (PCR) method described by Saiki et al.. in Science 239, 487 (1988), by Mullis et al. in U.S. Pat. No. 4,683,195 and by Sambrook, Fritsch and Maniatis (eds) in *Molecular Cloning, A Laboratory Manual*, Second Edition, Cold Spring Harbor Laboratory Press (1989). It is convenient to amplify the clones in commercially available lambda-gt11 vectors using lambda-gt11-specific oligomers as the amplimers.

Expressing DNA encoding IL-6 muteins

The DNA encoding the muteins of the invention may be replicated and used to express recombinant mutein following insertion into a wide variety of host cells in a wide variety of cloning and expression vectors.

The vector into which the DNA encoding the mutein IL-6 coding region is spliced may comprise segments of chromosomal, non-chromosomal and synthetic DNA sequences. Some suitable prokaryotic cloning vectors include plasmids from E. coli, such as colE1, pCR1, pBR322, pMB9, pUC, pKSM, and RP4. Prokaryotic vectors also include derivatives of phage DNA such as M13 and other filamentous single-stranded DNA phages.

Vectors for expressing the muteins of the invention in bacteria, especially E. coli, are also known. Such vectors include the PATH vectors described by Dieckmann and Tzagoloff in J. Biol. Chem. 260, 1513–1520 (1985). These vectors contain DNA sequences that encode anthranilate synthase (TrpE) followed by a polylinker at the carboxy terminus. Other expression vector systems are based on beta-galactosidase (pEX), lambda $P_L$; maltose binding protein (pMAL); glutathione S-transferase (pGST)—see Gene 67, 31 (1988) and Peptide Research 3, 167 (1990).

Vectors useful in yeast are available. A suitable example is the 2u plasmid.

Suitable vectors for use in mammalian cells are also known. Such vectors include well-known derivatives of SV-40, adenovirus, retrovirus-derived DNA sequences and vectors derived from a combination of plasmids and phage DNA.

Further eukaryotic expression vectors are known in the art (e.g., P. J. Southern and P. Berg, J. Mol. Appl. Genet. 1, 327–341 (1982); S. Subramani et al., Mol. Cell. Biol. 1, 854–864 (1981); R. J. Kaufmann and P. A. Sharp, "Amplification And Expression Of Sequences Cotransfected with A Modular Dihydrofolate Reductase Complementary DNA Gene," "J. Mol. Biol. 159, 601–621 (1982); R. J. Kaufmann and P. A. Sharp, Mol. Cell. Biol. 159, 601–664 (1982); S. I. Scahill et al., "Expression And Characterization Of The Product Of A Human Immune Interferon DNA Gene In Chinese Hamster Ovary Cells," Proc. Natl. Acad. Sci. USA 80 4654–4659 (1983); G. Urlaub and L. A. Chasin, Proc. Natl. Acad. Sci. USA 77, 4216–4220, (1980).

The expression vectors useful in the present invention contain at least one expression control sequence that is operatively linked to the DNA sequence or fragment to be expressed. The control sequence is inserted in the vector in order to control and to regulate the expression of the cloned DNA sequence. Examples of useful expression control sequences are the lac system, the trp system, the tac system, the trc system, major operator and promoter regions of phage lambda, the control region of fd coat protein, the glycolytic promoters of yeast, e.g., the promoter for 3-phosphoglycerate kinase, the promoters of yeast acid phosphatase, e.g., Pho5, the promoters of the yeast alpha-mating factors, and promoters derived from polyoma, adenovirus, retrovirus, and simian virus, e.g., the early and late promoters of SV40, and other sequences known to control the expression of genes in prokaryotic or eukaryotic cells and their viruses or combinations thereof.

Useful expression hosts include well-known prokaryotic and eukaryotic cells. Some suitable prokaryotic hosts include, for example, E. coli, such as E. coli SG-936, E. coli HB 101, E. coli W3110, E. coli X1776, E. coli X2282, E. coli DHI, and E. coli MRCl, Pseudomonas, Bacillus subtilis, and Streptomyces. Suitable eukaryotic cells include yeasts and other fungi, insect, animal cells, such as COS cells and CHO cells, human cells and plant cells in tissue culture.

Fusion Proteins

The muteins of the invention may be expressed in the form of a fusion protein with an appropriate fusion partner. The fusion partner preferably facilitates purification and identification. Increased yields may be achieved when the fusion partner is expressed naturally in the host cell. Some useful fusion partners include beta-galactosidase (Gray, et al., Proc. Natl. Acad. Sci. USA 79, 6598 (1982)); trpE (Itakura et al., Science 198, 1056 (1977)); protein A (Uhlen et al., Gene 23 369 (1983)); glutathione S-transferase (Johnson, Nature 338, 585 (1989)); Van Etten et al., Cell 58, 669 (1989)); and maltose binding protein (Guan et al., Gene 67, 21–30 (1987); Maina et al., Gene 74, 36–373 (1988); Riggs, P., in Ausebel, F. M. et al. (eds), Current Protocols in Molecular Biology, Greene Associates/Wiley Interscience, New York (1990)).

Such fusion proteins may be purified by affinity chromatography using reagents that bind to the fusion partner. The reagent may be a specific ligand of the fusion partner or an antibody, preferably a monoclonal antibody. For example, fusion proteins containing beta-galactosidase may be purified by affinity chromatography using an anti-beta-galactosidase antibody column (Ullman, Gene. 29, 27–31 (1984)). Similarly, fusion proteins containing maltose binding protein may be purified by affinity chromatography using a column containing cross-linked amylose; see Guan, European patent application 286,239.

Optionally, the DNA that encodes the fusion protein is engineered so that the fusion protein contains a cleavable site between the IL-6 mutein and the fusion partner. Both chemical and enzymatic cleavable sites are known in the art. The IL-6 mutant may occur at the amino-terminal or the carboxy terminal side of the cleavage site.

Suitable examples of sites that are cleavable enzymatically include sites that are specifically recognized and cleaved by collagenase (Keil et al., FEBS Letters 56, 292–296 (1975)); enterokinase (Hopp et al., Biotechnology 6, 1204–1210 (1988)); factor Xa (Nagai et al., Methods Enzymol. 153, 461–481 (1987)); and thrombin (Eaton et al., Biochemistry 25, 505 (1986)). Collagenase cleaves between proline and x in the sequence Pro-x-Gly-Pro wherein x is a neutral amino acid. Enterokinase cleaves after lysine in the sequence Asp-Asp-Asp-Asp-Lys. Factor Xa cleaves after arginine in the sequence Ile-Glu-Gly-Arg. Thrombin cleaves between arginine and glycine in the sequence Arg-Gly-Ser-Pro.

Specific chemical cleavage agents are also known. For example, cyanogen bromide cleaves at methionine residues in proteins.

Purifying Muteins

The recombinant protein is purified by methods known in the art. Such methods include affinity chromatography using specific antibodies. Alternatively, the recombinant protein may be purified using a combination of ion-exchange, size-exclusion, and hydrophobic interaction chromatography using methods known in the art. These and other suitable methods are described by Marston, "The Purification of Eukaryotic Proteins Expressed in *E. coli*" in *DNA Cloning*, D. M. Glover, Ed., Volume III, IRL Press Ltd., England, 1987.

Proper Folding

In order to achieve the correct, i.e. active, conformation of the IL-6 muteins, they must be folded properly. Proper folding requires the formation of the correct intramolecular disulfide bond (i.e. oxidation) between cysteine residues. Undesirable oxidation between intermolecular cysteine residues should be minimized.

Methods are known for oxidizing and refolding denatured proteins into an active state. Preferably, the protein concentration in the methods described below is less than 500 ug/ml during refolding and renaturation.

In one common method, the protein is dissolved in a six molar solution of a chaotrope such as guanidine hydrochloride, and the solution is diluted at least six-fold, preferably ten-fold. The dilute solution is then passed over a column, preferably a series of columns, and the mutant isolated. Some examples of suitable columns include at least one of an ion exchange, hydrophobic interaction, and/or gel filtration column.

In an alternative protocol, the mutein is dialyzed against, or diluted in, a buffer, such as 50 mM Tris HCl pH 8.5, 100 mM sodium chloride, 1 mM EDTA, in the absence of any reducing agent. The resulting dialysate is purified and fractionated by means of subsequent column retention and exclusion steps. Any of several well understood dialysis, oxidative and column fractionation protocols may be employed. For example, see "Methods in Enzymology, Volume 182—Guide to Protein Purification Deutscher, ed, Academic Press, San Diego, 1990."

A major advantage of an IL-6 mutein wherein the first and second cysteine residues are each replaced with other amino acid residues, while the third and fourth cysteine residues are retained, is that there is only one possible intramolecular cysteine-cysteine (cystine) disulfide bond that can be formed during the oxidation step. Moreover, there are fewer cysteine residues available for forming intermolecular disulfide bonds. This more selective oxidation step expedites the purification and isolation of the mutein.

Synergy between Truncation and Cysteine Removal

Brakenhoff et al. has suggested that the level of expression of an N-terminal deletion mutant of IL-6 (-28aa IL-6 CCCC) would be higher than that of full length IL-6, due to increased hydrophilicity of the deletion mutant. See Brakenhoff et al., J. Immunol. 139 4116–4121 (1987). It has unexpectedly been discovered that there is a particular advantage in both truncating the N-terminal end of native, mature IL-6 and substituting other amino acids for a pair of cysteine residues, especially the first and second cysteine residues. For example, a surprisingly high yield (10–15 mg per liter) of -22aa IL-6 XXCC, especially of -22aa IL-6 SSCC, is obtained when expressed in *E. coli*, even though no fusion protein is formed.

To illustrate the improved yields of truncated, cysteine-depleted muteins, DNA sequences encoding the following muteins were prepared and inserted into the expression vector pkk233-2 (Pharmacia) essentially as described in Examples 1–5:

-22aa IL-6 CCCC; -22aa IL-6 SSSS;

-22aa IL-6 SSCC; -22aa IL-6 CCSS;

IL-6 CCCC; IL-6 SSSS; IL-6 SSCC; and

IL-6 CCSS.

The expression vector pkk233-2 is described in Example 2.

The IL-6 molecules were expressed in *E. coli* strain HB101, solubilized with 6M urea, isolated, and assayed by ELISA in accordance with Example 11A. The results are shown in Tables 1 and 2.

Table 1 shows the effect on recovery levels of deleting the N-terminal 22 amino acids from the native IL-6 protein (CCCC) and from IL-6 mutants wherein one or both pairs of cysteine residues are replaced by serine residues (SSSS, SSCC, CCSS). Recovery levels are affected by components including transcription, translation, and stability factors. The level of recovery of each full length protein or mutein is arbitrarily assigned a value of 1, and the relative recovery level of the corresponding truncated protein or mutein given.

The results show that each truncated protein or mutein is recovered at an approximately 2–50 fold higher level than the corresponding full length protein or mutein.

TABLE 1

Relative Recovery Levels of Truncated
and Full Length IL-6 Proteins and Muteins

| IL-6 Protein/Mutein | Relative Recovery Level[1] |
|---|---|
| CCCC | 2.4 |
| SSSS | 18.2 |
| SSCC[2] | 10.6 |
| CCSS | 46.5 |

[1]Ratio of Expression of truncated to full length protein or mutein.
[2]Full length and truncated mutein in according with the invention.

As can be seen, the effect is greatest for the muteins, in which at least one pair of cysteine residues is replaced by serine residues.

Table 2 shows the effect on relative recovery levels of replacing at least one pair of cysteine residues with serine residues in the full length or truncated IL-6 sequences, IL-6 CCCC or -22aa IL-6 CCCC, respectively. In this comparison, the recovery levels obtained in according with the procedure described in Example 11A of both the full length and truncated IL-6 proteins are arbitrarily assigned a value of 1. In the first column of numbers in Table 2, the relative recovery levels of the full length cysteine-free (SSSS) and cysteine-depleted (SSCC and CCSS) muteins are given as the ratio of their respective levels of recovery to that of full length, native IL-6 (IL-6 CCCC). Similarly, in the second column of numbers in Table 2, the relative recovery levels of the truncated cysteine-free (SSSS) and cysteine-depleted (SSCC and CCSS) IL-6 muteins are given as the ratio of their respective levels of recovery to that of truncated, native IL-6 (- 22aa IL-6 CCCC).

Consider the first column of numbers in Table 2. As can be seen, replacement of one or both pairs of cysteine residues results in an 8–34 fold increase in recovery level relative to the recovery level of full length, native IL-6.

Unexpectedly, this effect is amplified when the N-terminal 22 amino acids are deleted. Thus, the second column of numbers in Table 2 demonstrates that the replacement of one or both pairs of cysteine residues in the truncated, native IL-6 sequence results in a 100–160 fold increase in recovery level.

It can be seen from Table 1 that there is a 2.4 fold increase in recovery level of the truncated IL-6 protein (-22aa IL-6 CCCC) relative to the full length IL-6 protein (IL-6 CCCC). When this increase is taken into account, the recovery level of the truncated, cysteine-free (-22aa IL-6 SSSS) and cysteine-depleted (-22aa IL-6 SSCC and -22aa IL-6 CCSS) IL-6 muteins is estimated to be approximately 250–400 times greater than native, full length IL-6 CCCC. The recovery level of -22aa IL-6 SSCC, which, as explained above exhibits unexpectedly high activity, is as much as 250–400 fold higher than that of full length, native IL-6.

TABLE 2

Relative Recovery Levels of Native IL-6
and Cysteine-free and Cysteine-depleted IL-6 Muteins

| IL-6 Sequence | Relative Recovery Level of Full Length Sequence[1] | Relative Recovery Level of Truncated Sequence[2] |
|---|---|---|
| CCCC | 1.0 | 1 |
| SSSS | 8.3 | 160 |
| SSCC[3] | 33.5 | 147 |
| CCSS | 14.4 | 109 |

[1]Ratio of recovery level of cysteine-free (SSSS) and cysteine-depleted (SSCC and CCSS) full length muteins to recovery of level of native, full length IL-6 protein (CCCC).
[2]Ratio of recovery level of cysteine-free (SSSS) and cysteine-depleted (SSCC and CCSS) truncated muteins to recovery level of native, truncated IL-6 protein (CCCC).
[3]Full length and truncated muteins in accordance with the invention.

The recovery levels of the eight different IL-6 molecules reported in Tables 1 and 2 were induced to refold by dilution in PBS and dialysis. Table 3 shows the percent recovery of refolded IL-6 as compared to the levels extracted in 6M urea.

It can be seen that both full length, native IL-6 CCCC and the full length mutein IL-6 SSCC molecules can be refolded to approximately the same extent (35% and 44%, respectively). Only 13% to 15% of the full length cysteine-free mutein IL-6 SSSS and the full length cysteine-depleted IL-6 CCSS mutein can be refolded properly.

The truncated versions of these molecules follow the same pattern. The -22aa IL-6 CCCC and -22aa IL-6 SSCC truncated muteins were recovered at a level of 19–26% relative to the levels extracted in 6M urea. The recovery of -22aa IL-6 CCSS and -22aa IL-6 SSSS was only approximately 5% relative to the levels extracted in 6M urea.

TABLE 3

Recovery of Refolded IL-6 from its Denatured Form

| Sequence | Percent Recovery of Full Length Sequence[1] | Percent Recovery of Truncated Sequence[2] |
|---|---|---|
| CCCC | 35 | 19 |
| SSSS | 15 | 5 |
| SSCC[3] | 44 | 26 |
| CCSS | 13 | 6 |

[1]Percent recovery of full length IL-6 protein and muteins by dilution and dialysis relative to amount present in 6M urea.
[2]Percent recovery of truncated IL-6 protein and muteins lacking N-terminal 22 amino acids by dilution and dialysis relative to amount present in 6M urea.
[3]Full length and truncated mutein of the invention.

It is apparent from its unexpected activity, level of recovery, and recovery following refolding that -22aa IL-6 SSCC is a preferred mutein in accordance with the present invention. Similar superior combinations of properties are expected with truncations of 4–28, preferably 12–28, and more preferably 22–28. In addition, similar superior combinations of properties are expected when the cysteine residues in truncated IL-6 muteins corresponding to positions 45 and 51 of full length, native IL-6 are substituted by amino acid residues other than two serine residues. Preferably, the other amino acid residues are neutral amino acids, preferably alanine, threonine, proline, or glycine, and more preferably alanine.

Utility

The IL-6 muteins of the invention are useful in the in vitro and in vivo regulation of cells. For example, the IL-6 muteins stimulate the proliferation and differentiation of B cells, T cells, megakaryocytes, and multipotential hematopoietic progenitor cells. The stimulation of proliferation of megakaryocytes leads to the production of platelets. In addition, the IL-6 muteins induce various acute phase proteins in liver cells.

As a result of the biological activities described above, the IL-6 muteins are useful in immunotherapeutic and anti-inflammation compositions. The muteins may also be used for the treatment of patients suffering from thrombocytopenia and patients undergoing chemotherapy or bone marrow transfers.

EXAMPLES

Example 1. Plasmid expressing fusion protein containing Cysteine free IL-6. pBgal/EK/cfIL-6.

The plasmid pBgal/EK/cfIL-6, which is illustrated as FIG. 3, contains a DNA sequence that encodes a fusion protein comprising beta-galactosidase, followed by an enterokinase cleavage site, which is, in turn, followed immediately by a synthetic IL-6 peptide sequence. The cfIL-6 peptide sequence is that of native IL-6, except that the four cysteine residues, which occur at positions 45, 51, 74, and 84 of the mature full length IL-6 molecule, are replaced by serine residues and the first amino acid residue (alanine) is missing, i.e. -1aa IL-6 SSSS. (The mature IL-6 molecule is defined for the purpose of this application as starting with Ala Pro Val Pro.) In pBgal/EK/cfIL-6, a truncated 0.580 kb cysteine-free IL-6 sequence lacking the first four N-terminal amino acids is surrounded by Eco RII and Hind III restriction sites. The sequence of the 0.580 kb IL-6 fragment is shown as FIG. 2.

pBgal/EK/cfIL-6 may be prepared by the method described in PCT application WO 90/06370. pBgal/EK/cfIL-6 was also deposited in the American Type Culture Collection, Rockville, Md., on Nov. 30, 1989, accession number ATCC 68187.

Example 2. Vector encoding full length IL-6 in non-fusion format. pKK233-2 cfIL-6

The pBgal/EK/cfIL-6 vector (FIG. 3) described in section 5.10.2 of PCT international patent application W090/06370 is digested with the enzymes EcoRII and HindIII. The vector is digested with 20 units of each enzyme per 20 ug of plasmid at 37° C. for two hours in the following buffer: (50 mM Tris.HCl pH 7.4, 6 mM MgCl2, 50 mM KCl, 50 mM NaCl and 1 mM dithiothreitol (DTT)). The 0.580 Kb EcoRII/HindIII IL-6 fragment is isolated by electro-elution. This fragment will be referred to as Sequence A. The IL-6 encoded by sequence A lacks the nucleotides for the first four N-terminal amino acids of full length, mature IL-6, Ala Pro Val Pro. In addition, all four cysteines in native IL-6 have been replaced by serine residues, i.e. -4aa IL-6 SSSS (SEQ ID NO: 3 and SEQ ID NO: 4).

The expression vector pKK233-2 is available from Pharmacia. The transcription unit in pKK233-2 contains the strong trc promoter (P$_{trc}$), the lacZ' ribosome binding site, a unique Nco I site at the ATG start codon and two rRNA transcription terminators, See Amann and Brosius, Gene 40, 183 (1985).

Sequence A is inserted into the polylinker of the pKK233-2 expression vector. In order to do so, the pKK233-2 expression vector (20 ug) is cut with Nco I and HindIII in the presence of 50 mM Tris.HCl pH 8.0, 10 mM MgCl2, and 100 mM NaCl. The approximately 4.6 Kb vector fragment is isolated and will be referred to as Sequence B.

In order to restore the four amino acids of IL-6 missing from Sequence A to the final product and to join Sequence A to Sequence B, a synthetic double-stranded oligonucleotide, Sequence C, is prepared. The oligonucleotide is made with NcoI and EcoRII overlapping sites and allows the IL-6 fragment Sequence A to be in frame with the vector fragment Sequence B. The sequence of oligonucleotide C (SEQ ID NO: 9 and SEQ ID NO: 10, including the amino acid sequence SEQ ID NO: 11) is:

```
5'  CATGGCTCCGGTTCCG  3'
3'      CGAGGCCAAGGCGGTCC  5'
        M   A   P   V   P
```

One ug of each strand of Sequence C is treated with 10 to 20 units of polynucleotide kinase in the presence of 1 mM rATP in a buffer containing: 50 mM Tris HCl pH 7.6, 10 mM MgCl2, 5 mM DTT, 0.1 mM spermidine and 0.1 mM EDTA, at 37° C. for 45 minutes. The volume of the reaction mixture is 25 ul. Ten µl of annealing buffer (50 mM Tris HCl pH 7.8 and 10 mM MgCl2) is added to the 25 µl kinase reaction mixture, which is then heated to 100° C. for five minutes, followed by slow cooling to 25° C.

Figure 4:
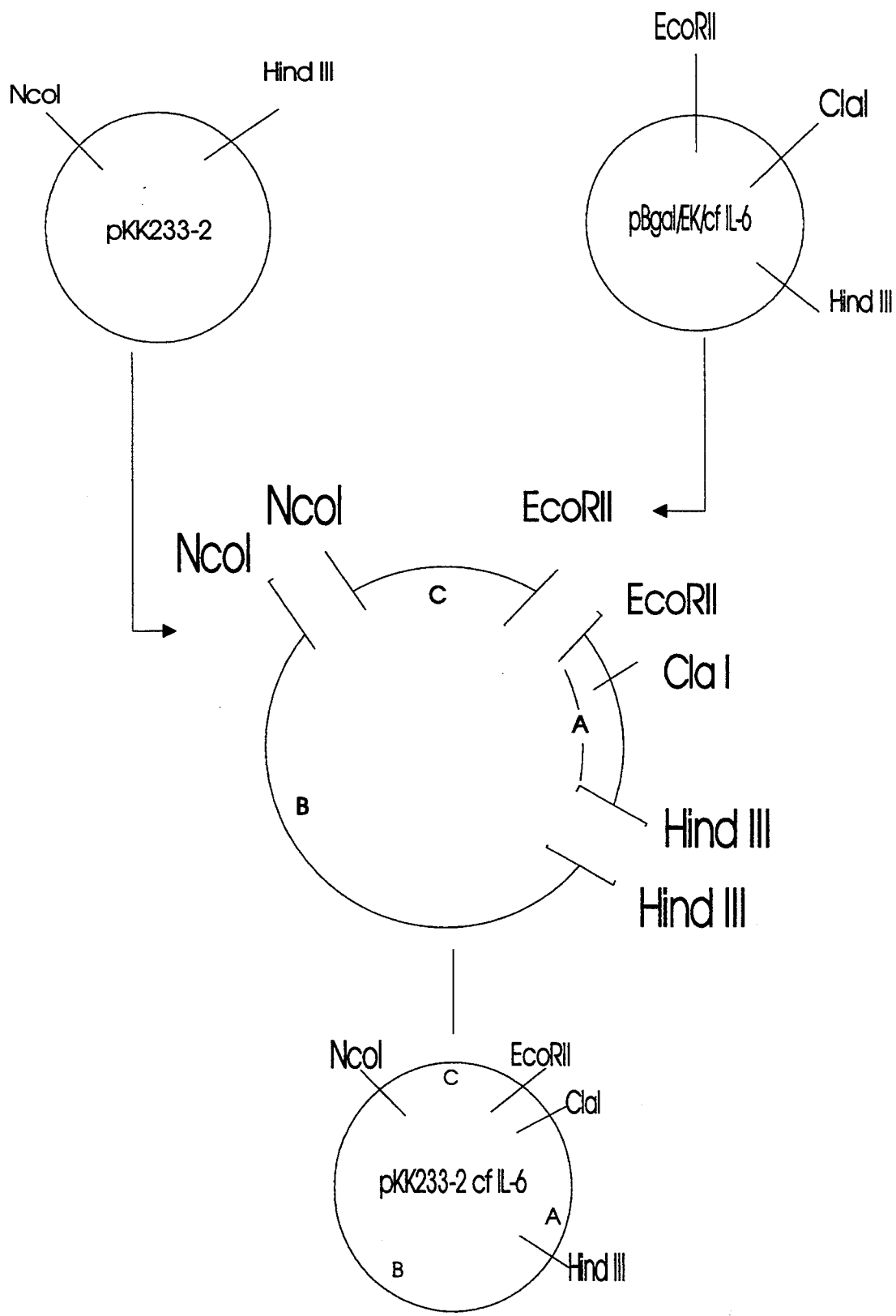
FIG. 4 shows the construction of the plasmid described in Example 2 as pKK233-2cfIL-6.

To ligate Sequences A, B and C, one pmole each of Sequence B and C was co-precipitated with three pmoles of Sequence A. Ligation is accomplished in a 20 ul reaction mixture containing 20 mM Tris HCl, pH 7.6, 0.5 mM rATP, 10 mM MgCl2, 5 mM DTT and one unit of T4-induced ligase at 16° C. for 16 hours. Ten microliters of this ligation reaction mixture is then added to competent HB101 and JM101 cells. Ampicillin-resistant colonies are selected after overnight incubation at 37° C. The ampicillin-resistant clone is verified as having the IL-6 gene by restriction enzyme analysis, sequencing data (Sanger, et al., 1977 Proc. Nat. Acad. of Sci., 74:5463) and expression of the IL-6 protein. The clone derived from the above procedure is called pKK233-2 cfIL-6. See FIG. 4.

Example 3. Vector encoding cysteine-free IL-6 lacking 22 N-terminal amino acids in non-fusion format—pKK-22aa cfIL-6

The Bgal/EK/cf IL-6 vector is digested with the enzymes Cla I and HindIII in the following buffer: 50 mM Tris-HCl pH 8.0, 10 mM MgCl2 and 50 mM NaCl. A 0.52 Kb IL-6 fragment is isolated as described above, and called Sequence D; see FIG. 3. The Sequence D fragment creates an IL-6 sequence with the first 26 amino acids removed when ligated to Sequence E, which is described below.

A synthetic oligonucleotide called Sequence E is prepared with overlapping NcoI and Cla I sites and sequence information to restore amino acid residues 23–26. The sequence of oligonucleotide E (SEQ ID NO: 12 and SEQ ID NO: 13) is:

```
5'  CATGTCCGAACGTAT  3'
3'      AGGCTTGCATAGC  5'
```

The oligonucleotide is kinased and annealed as described in example 2 above.

Figure 5:
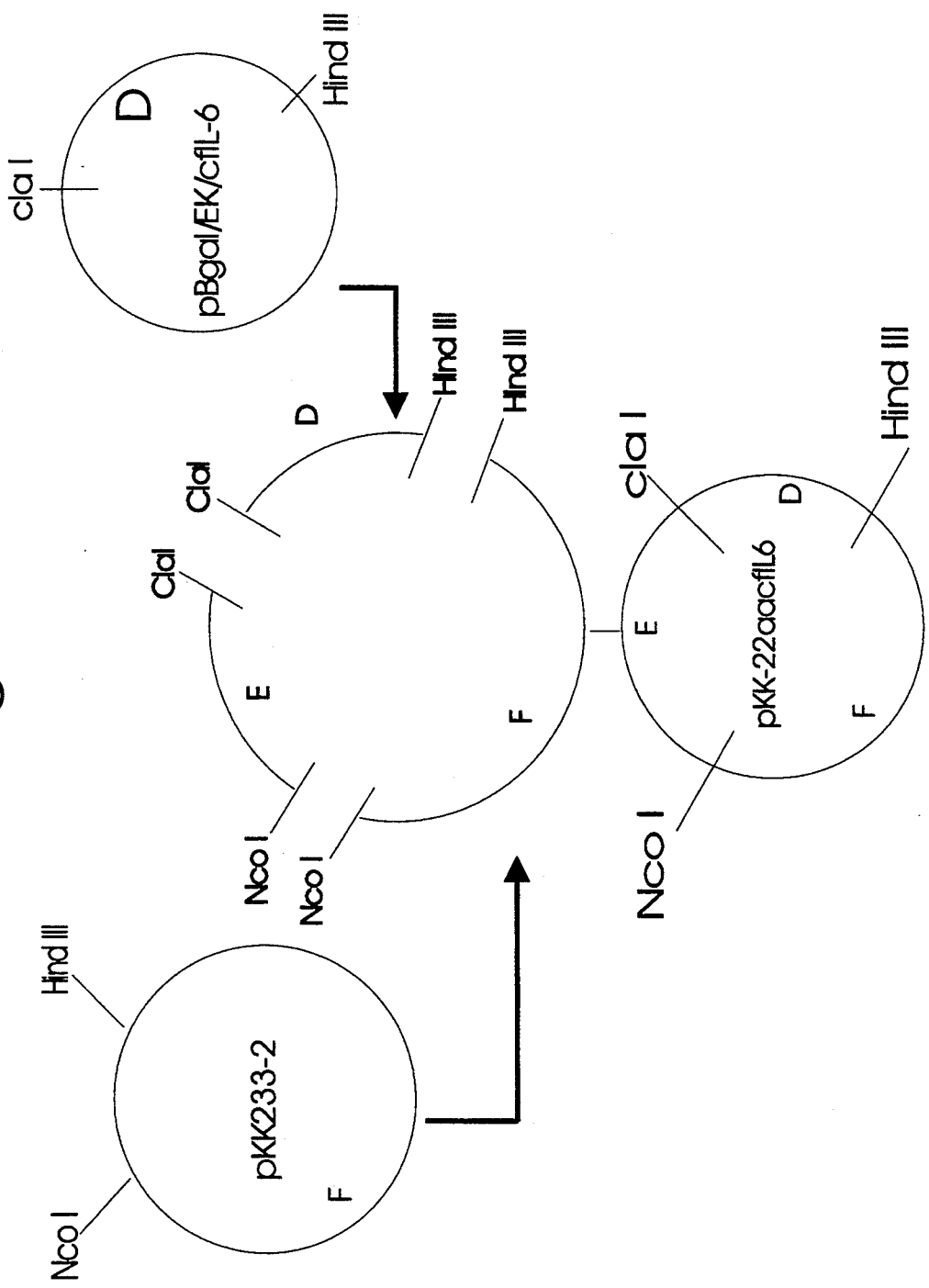
FIG. 5 shows the plasmid described in Example 3 as pKK-22aa cfIL-6.

The pKK233-2 vector is digested with the enzymes NcoI and HindIII, and the larger fragment, called fragment F is isolated. The ligation of fragments D, E, and F is performed as described in example 2 above with the fragment ratios being 3 pmoles: 1 pmole: 1 pmole, respectively. The clone derived from this ligation is called pKK-22aa cfIL-6. The truncated IL-6 sequence starts at the 23rd amino acid residue of the full length, cysteine-free IL-6 (Ser Glu Arg, etc.). See FIG. 5.

Example 4. Restoration of the third and fourth cysteine residues in cysteine-free IL-6 lacking the amino terminal 22 amino acids. -22aa IL-6 SSCC.

The codons for the serine residues at positions corresponding to codons 74 and 84 of IL-6 in pKK-22aa cfIL-6 are replaced with codons for cysteine residues using an in vitro mutagenesis procedure commercially available from Promega Corp. called "Altered Sites in vitro Mutagenesis System." The manual supplied by Promega is available from the file history of this specification in the United States Patent and Trademark Office. The codons for the serine residues at positions 45 and 51 are retained.

The procedure involves digesting the pKK233-2 cfIL-6 vector with an EcoRI enzyme in the following buffer: 50 mM Tris-HCl pH 8.0, 10 mM MgCl₂ and 100 mM NaCl. The 0.75 Kb IL-6 fragment, called Sequence G, is isolated. The pSelect vector provided by Promega is digested with EcoRI and the 5.7 Kb vector, called Sequence H, is isolated. The IL-6 fragment G is ligated to the pSelect vector H in a ratio of 3 pmoles:1 pmole, respectively. Clones are selected for tetracycline resistance and a positive IL-6 clone, called pSelect-IL-6 is identified by restriction enzyme analysis to verify that the IL-6 insert is in the correct orientation. Single-stranded pSelect-IL-6 DNA is prepared according to the Promega instructions. A synthetic oligonucleotide, called Sequence I, which contains codons for cysteine at positions corresponding to 74 and 84 of mature, native IL-6, is prepared. The sequence of oligonucleotide I (SEQ ID NO: 14) is:

residues at the positions corresponding to amino acids 45 and 51 of full length, native IL-6, i.e, -22aa IL-6 SSCC, is expressed in high yield upon induction with isopropyl-beta-D-thiogalactopyranoside in *E. coli* strains HB101 and JM101.

Example 5. Alternative Restoration of the third and fourth cysteine residues in cysteine-free, full length IL-6. pKK IL-6 SSCC The pKK-22aa IL-6 SSCC clone from Example 4 is digested with ClaI and Bgl II. Three pmoles of the resulting 0.43 kb fragment is ligated to 1 pmole of the larger fragment obtained by digesting pKK233-2 cfIL-6 (Example 2 and FIG. 4) with Cla I and Bgl II. The resulting plasmid, which is called pKK233-2 IL-6 SSCC, expresses full length IL-6 containing the third and fourth cysteine residues in *E. coli* strains HB101 and JM101. The NcoI/Hind III fragment of pKK233-2, which encodes IL-6 SSCC, is shown as FIG. 6.

Example 6. Enhanced expression of IL-6 containing serine residues at positions 45 and 51 and lacking 22 N-terminal amino acids. pV₃-22aa IL-6 SSCC The pGem-1 vector from Promega is modified to have only a NcoI and KpnI cloning site between the original Hind III and Eco RI multiple cloning sites. This is accomplished by placing an oligonucleotide between the Eco RI and Hind III sites. The sequence of the oligonucleotide (SEQ ID NO: 15 and SEQ ID NO: 16) is:

```
5' CCGAAGATGGCTGAAAAAGATGGATGTTTTCAATCTGGAT
   TCAATGAGGAAACTTGTCTGGTGAAAATCATCACAGGCCTT 3'
```

```
5' AGCTTGGTACCACACCATGGATGTATATCTCCTTCTTAAAGTTAAA
3'     ACCATGGTGTGGTACCTACATATAGAGGAAGAATTTCAATTT

CAAAATTATTTCTAGG 3'
       GTTTTAATAAAGATCCTTAA 5'
```

The underlined nucleotides code for the third and fourth cysteine residues at positions that correspond to positions 74 and 84 in mature, native IL-6.

The mutagenesis procedure was carried out according to the Promega procedure. Clones from this mutagenesis are initially selected on both ampicillin and tetracycline plates. The clones are identified as containing the cysteines by directly sequencing the positive drug resistant clones.

The resulting vector is called pV₂. To enhance expression, an oligonucleotide is made with two Shine-Dalgarno sequences and an overlapping EcoRI site at one end and an overlapping NcoI site at the other end. These overlapping ends allow the Shine-Delgarno sequence to be inserted directly upstream from one AUG translational start site in pV2. The sequence of the oligonucleotide (SEQ ID NO: 17 and SEQ ID NO: 18) is:

```
5' CATGGTTTAAACCTCCTTACTAATCGATACCCTTTTTACGTGAACTTG 3'
3'     CAAATTTGGAGGAATGATTAGCTATGGGAAAAATGCACTTGAACTTAA 5'
```

The plasmid identified as containing both cysteines is digested with ClaI and BglII enzymes in the following buffer: 50 mM Tris-HCl pH 8.0, 10 mM MgCl₂ and 50 mM NaCl. The resulting 0.43 Kb IL-6 fragment is isolated. Three pmoles of this IL-6 fragment is ligated to one pmole of the 4.8 Kb fragment isolated after digesting pKK-22aa cfIL-6 (Example 2 and FIG. 4) with ClaI and BglII. This ligation reaction is added to competent HB101 and JM101 cells. Ampicillin-resistant clones are isolated and verified as containing DNA encoding IL-6 muteins having cysteines at position 74 and 84 by sequence analysis and ultimately IL-6 protein production. The clone containing the plasmid, which is called pKK-22aa IL-6 SSCC, expresses IL-6 containing these cysteine residues and lacking the amino terminal 22 amino acids in *E. coli* strains HB101 and JM101. IL-6 that lacks the N-terminal 22 amino acids and that contains serine The modified V₂ vector with the above oligonucieotide is called pV3. The -22aa IL-6 SSCC fragment is isolated from the pKK-22aa IL-6 SSCC clone (Example 4) at the ClaI/Hind III sites (Sequence D modified by having cysteine residues at positions corresponding to 74 and 84 of native IL-6). The IL-6 fragments D and E are ligated to the pV₃ vector, which is also digested with Nco I and Hind III; see FIG. 5 and Example 3. The ampicillin resistant clone obtained from this ligation is called pV3-22aa IL-6 SSCC, and is expressed in *E. coli* strain BL21 (N.Y. State Research Foundation and Brookhaven Laboratories). A derivative of BL21, JM109 (DE3), which is available from Promega, is also suitable. The -22aa IL-6 SSCC from Example 6 is solubilized as in Example 8 and purified by the method of Example 9A, 11B, or 11C.

Example 7. Growth of *E. coli* strain HB101 containing pKK-22aa IL-6 SSCC.

A one-liter culture of HB101 cells containing pKK-22aa IL-6 SSCC is started from a frozen stock. The culture is grown overnight at 37° C. in LB medium. A ten-liter fermentor containing M9 media is inoculated with the overnight culture. When the culture reaches an absorbance of 0.5 at 595 nm (approximately $10^7$ CFU/ml), it is induced with 0.5 mM isopropyl-beta-D-thiogalactopyranoside (IPTG). After four hours of induction the cells are harvested. The final wet weight yield is about 10 g of cell paste per liter.

Example 8. Preparation of Bacterial Lysate for Isolation of pKK-22aa IL-6 SSCC

The recombinant cell lysate from pV3-22aa IL-6 SSCC or pKK-22aa IL-6 SSCC is prepared by resuspending the cell paste obtained in Example 6 or 7, respectively, in 20 mM Tris-HCl pH 8.0, 50 mM NaCl, 10 mM EDTA, 0.1 mM phenylmethylsulfonyl fluoride (PMSF) (TNE buffer) and incubating with lysozyme for 15 minutes on ice. Following the incubation with lysozyme, the suspension is sonicated on ice and then centrifuged at 5000×g for 30 minutes. The resulting pellet is washed twice with TNE buffer containing 1% Triton X-100. The supernatants are discarded. The pellet containing -22aa IL-6 SSCC inclusion bodies is suspended in 6M guanidine hydrochloride, 1 mM EDTA, 50 mM Tris-HCl pH 8.5. The presence of -22aa IL-6 SSCC was confirmed by ELISA.

Example 9A. Purification of -22aa IL-6 SSCC

The solubilized -22aa IL-6 SSCC extract from Example 8 is refolded by dialysis against 20 mM Tris-HCl pH 8.5, 100 mM NaCl, 1 mM EDTA and the resulting insoluble material removed by centrifugation. The dialyzed extract is adjusted to 45% saturation with ammonium sulfate and allowed to precipitate for two hours at 4° C. The -22aa IL-6 SSCC remains in the soluble fraction while the majority of *E. coli* contaminants are precipitated and removed by centrifugation.

For initial characterization of the -22aa IL-6 SSCC molecule, refolded extract is purified by reverse-phase chromatography. The sample is loaded onto a Vydac $C_{18}$ column and eluted with a linear gradient of 10%–90% $CH_3CN/0.1\%TFA/H_2O$. Two samples (R4 28 and R4 29) containing the purified -22aa IL-6 SSCC are assayed for biological activity in the B9 and SKW 6.4 assays; see Example 12.

Example 9B. Preparation of pKK -22aa IL-6 AACC

The codons for the serine residues at positions 45 and 51 in the pKK-22aa IL-6 SSCC clone were replaced by alanine residues using an in vitro mutagenesis procedure commercially available from Promega Corp. as described in Example 4. The procedure involves digesting pKK-22aa IL-6 SSCC with the restriction enzymes Hind III and ClaI in the following buffer: 50 mM potassium acetate, 20 mM tris-acetate ph 7.9, 10 mM magnesium acetate, 1 mM DTT. The 0.52 kb IL-6 fragment is isolated. The tetracycline resistant pSelect vector provided by Promega is digested with Cla I and Hind III in the buffer described above and the 5.3 kb pSelect vector fragment is isolated. The 0.52 kb IL-6 fragment is ligated to the 5.3 kb pSelect vector fragment in a ratio of 3:1 pmoles, respectively. Clones are selected for tetracycline resistance and a pSelect IL-6 clone, called pSelect-IL-6 (Cla/Hind) is identified by restriction analysis. Single stranded pSelect IL-6 (Cla/Hind) is prepared according to the Promega instructions. A synthetic oligonucleotide that contains codons for alanine at positions 45 and 51 is prepared. The sequence of the synthetic oligonucleotide (SEQ ID NO: 19) is:

```
5' TGCCAGTGCTTCTTT
   ACTCTTGTTAGCGGT

ACTGCTTTCTGCCATGTT
   CTCTTTTCTCAGCGCTGATAT 3'
```

The mutagenesis procedure was carried out according to the Promega procedure. Clones from one mutagenesis are initially selected on both ampicillin and tetracycline plates. The clones are identified as containing the alanines by directly sequencing the positive drug resistant clones.

The pSelect IL-6 plasmid containing both alanines is digested with the enzymes Hind III and ClaI as described above. The 0.52 kb fragment encoding IL-6 is isolated. The pKK-22aa IL-6 SSCC vector is digested with ClaI and Hind III, and the 4.6 kb fragment is isolated. Three pmoles of the 0.52 kb IL-6 fragment is ligated to the 4.6 kb pkk-22aa IL-6 SSCC fragment to form pkk-22aa IL-6 AACC. Ampicillin-resistant clones are isolated and verified as containing DNA encoding an IL-6 mutein having alanine at positions 45 and 51 by sequence analysis and, ultimately, by IL-6 protein production. -22aa IL-6 AACC is expressed by the method described in examples 6–8 and purified by the method described in examples 9A, 11B, or 11C.

Figure 7:
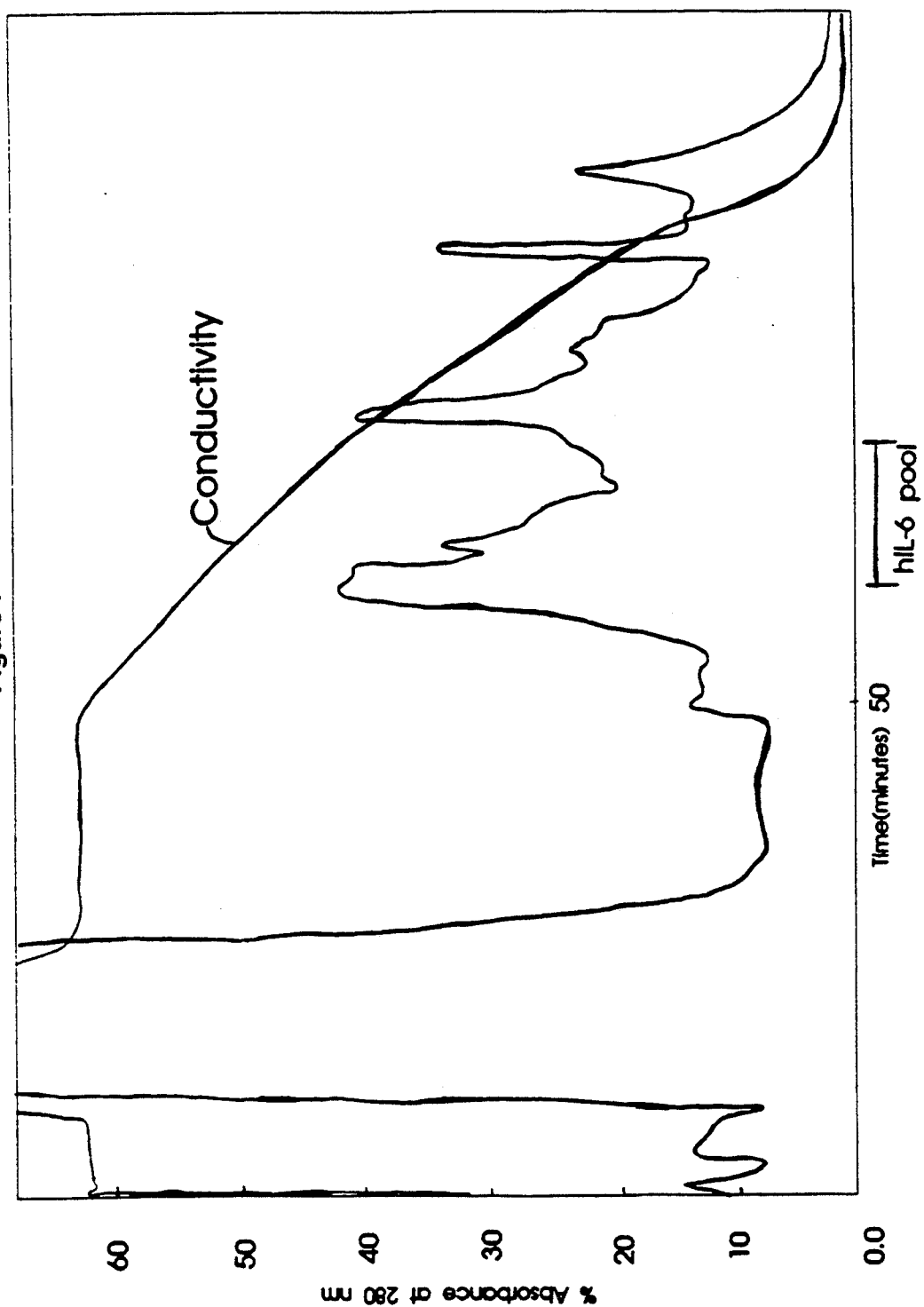
Figure 8:
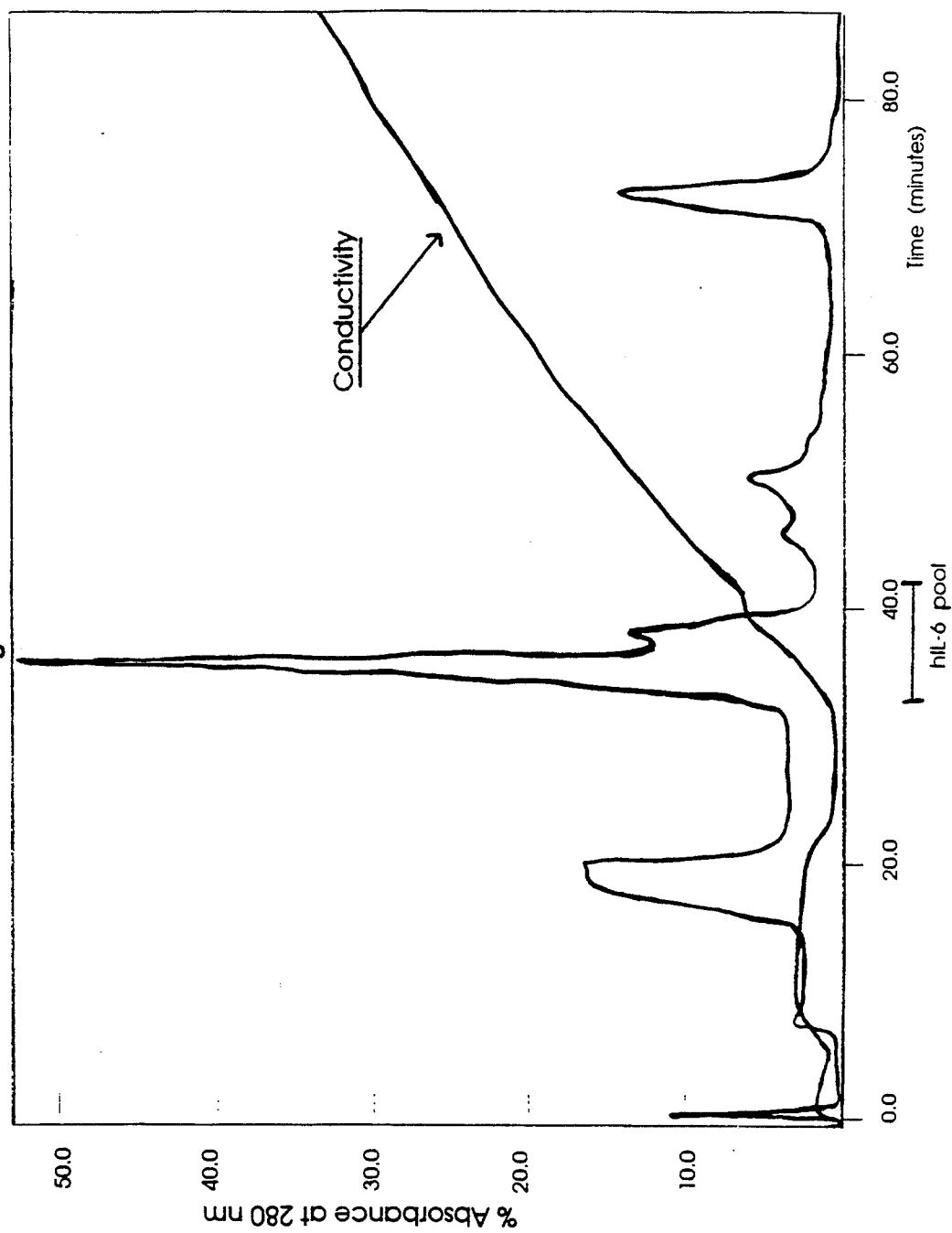
FIG. 8 shows a chromatogram of the elution of -22aa IL-6 SSCC from a Q-sepharose column. The absorbance of the fractions at 280 nm versus time in minutes and the gradient profile of conductivity is compared; see Example 10b.
Figure 9:
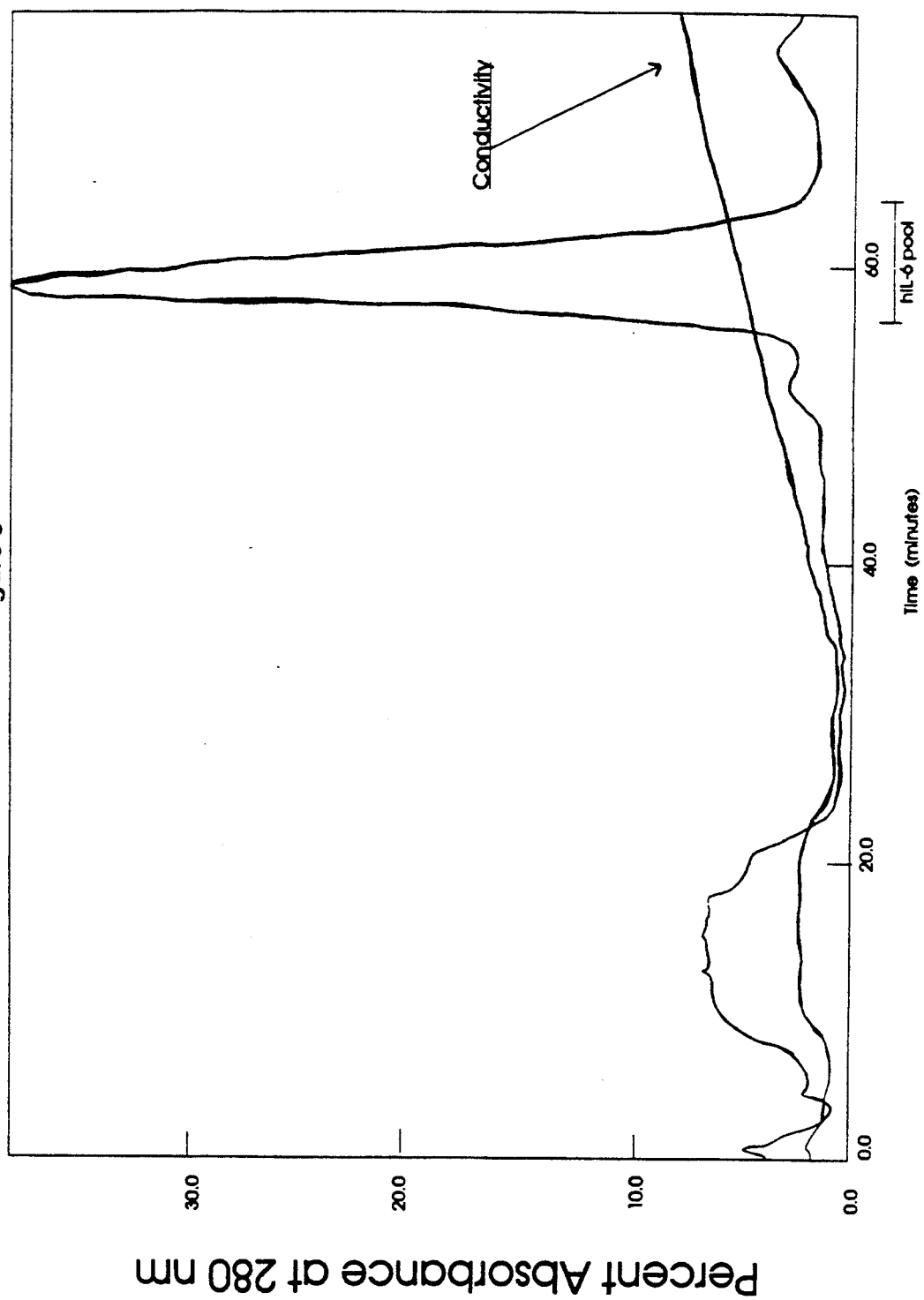
FIG. 9 shows a chromatogram of the elution of -22aa IL-6 SSCC from a CM-sepharose ion exchange column. The absorbance of the fractions at 280 nm versus time in minutes and the gradient profile of conductivity is compared; see Example 10c.

Example 10. HPLC for Large-Scale Purification of -22aa IL-6 SSCC a. The ammonium sulfate precipitated extract from Example 9A is loaded onto a Phenyl-sepharose hydrophobic interaction column equilibrated with 1.7M $(NH_4)_2SO_4$, 20 mM Tris-HCl pH 7.4. The column is eluted with a linear gradient of 20 mM Tris-HCl pH 7.4 and the fractions containing -22aa IL-6 SSCC are pooled (FIG. 7).

b. The Phenyl-sepharose pool is desalted on a G-25 column and then loaded onto a Q-sepharose column equilibrated with 20 mM Tris-HCl pH 8.0. The column is eluted with a linear gradient of 500 mM NaCl and fractions containing -22aa IL-6 SSCC are pooled (FIG. 8).

c. The Q-sepharose pool is loaded onto a CM-sepharose ion exchange column equilibrated with 20 mM sodium acetate, pH 6.0. The column is eluted with a linear gradient of 500 mM sodium acetate, pH 7.0 and the -22aa IL-6 SSCC containing fractions are pooled (FIG. 9).

Example 11. Characterization of Purified -22aa IL-6 SSCC

The -22aa IL-6 SSCC is produced in Examples 8–10 as an inclusion body with >95% of the human IL-6 activity remaining in the insoluble fraction after cell lysis. The mutein is solubilized with the chaotrope guanidine-HCl and then refolded by removal of the chaotrope. Cell lysates subjected to SDS-PAGE under reducing conditions show the appearance of a single 18 kd band that can be detected by monoclonal anti-hIL-6 in Western blots, but not detected in control lysates. The pI of -22aa IL-6 SSCC is ~6.7 as determined by isoelectric focusing.

The -22aa IL-6 SSCC purified by the method described above was >95% pure as determined by SDS-PAGE, Western blot, and N-terminus sequencing analysis. The sequencing analysis shows that the first 13 amino acids are identical to the predicted sequence and indicates that less than 10% of the purified -22aa IL-6 SSCC species contains an N-terminal methionine residue. In addition, amino acid analysis confirms that the mutein -22aa IL-6 molecule contains two cysteine residues.

Example 11A. Production, Isolation and Determination of IL-6 molecules for Comparison of Recovery Levels. See Tables 1-3

Induction and Extraction:

Fifty ml cultures of *E. coli* strain HB101, each containing DNA encoding a different full length or truncated, cysteine-containing, cysteine-free, or cysteine-depleted IL-6 molecule in the expression vector pkk233-2 (see Examples 1-5) were grown at 37° C. with shaking in M9 media supplemented with casamino acids and thiamine. At an absorbance of 0.4 at 600 nm, the cultures were induced with 1 mM isoProPyl-beta-D-thiogalactopyranoside (IPTG) for four hours. The cells were harvested at 3000 rpm and the pellet was resuspended in 1 ml of 50 mM Tris-HCl pH 8.0 containing 1 mM PMSF. Lysozyme was added to the cells at a final concentration of 75 ug/ml and then left on ice for 15 minutes. Pancreatic DNAse and $MgCl_2$ were then added at a final concentration of 75 ug/ml and 65 mM, respectively. Incubation was continued at 37° C. for another 45 minutes. The total cell extract was brought up to 6M urea by adding solid urea and then briefly sonicated. The mixture was then centrifuged at 13,000 rpm and the supernatant containing the solubilized proteins was collected. No IL-6 was detected in the residual pellet.

To facilitate refolding, the 6M urea solubilized protein solutions were immediately diluted to 1M urea with phosphate buffered saline (PBS) containing 1 mM DTT and then dialyzed against PBS/DTT at room temperature overnight with three changes of dialysis buffer (1 L each). The protein solution was clarified by centrifugation at 10,000 rpm, and protein concentrations in the supernatants were determined by a Bio-Rad protein assay (Bio-Rad, Richmond, Calif.).

IL-6 Determination:

The total cell extracts and refolded proteins were assayed by ELISA using the Quantikine IL-6 assay kit (R&D Systems, Minneapolis, Minn.). Briefly, a monoclonal antibody specific for IL-6 coated onto a microtiter plate was used to capture any IL-6 contained in each sample. After washing, an enzyme linked polyclonal antibody specific for IL-6 was added to allow detection of any bound IL-6. Optical density values of samples were recorded (using a microtiter plate reader from Hewlett Packard) and compared to those of an IL-6 standard curve (10-2000 pg/ml).

Figure 9A:
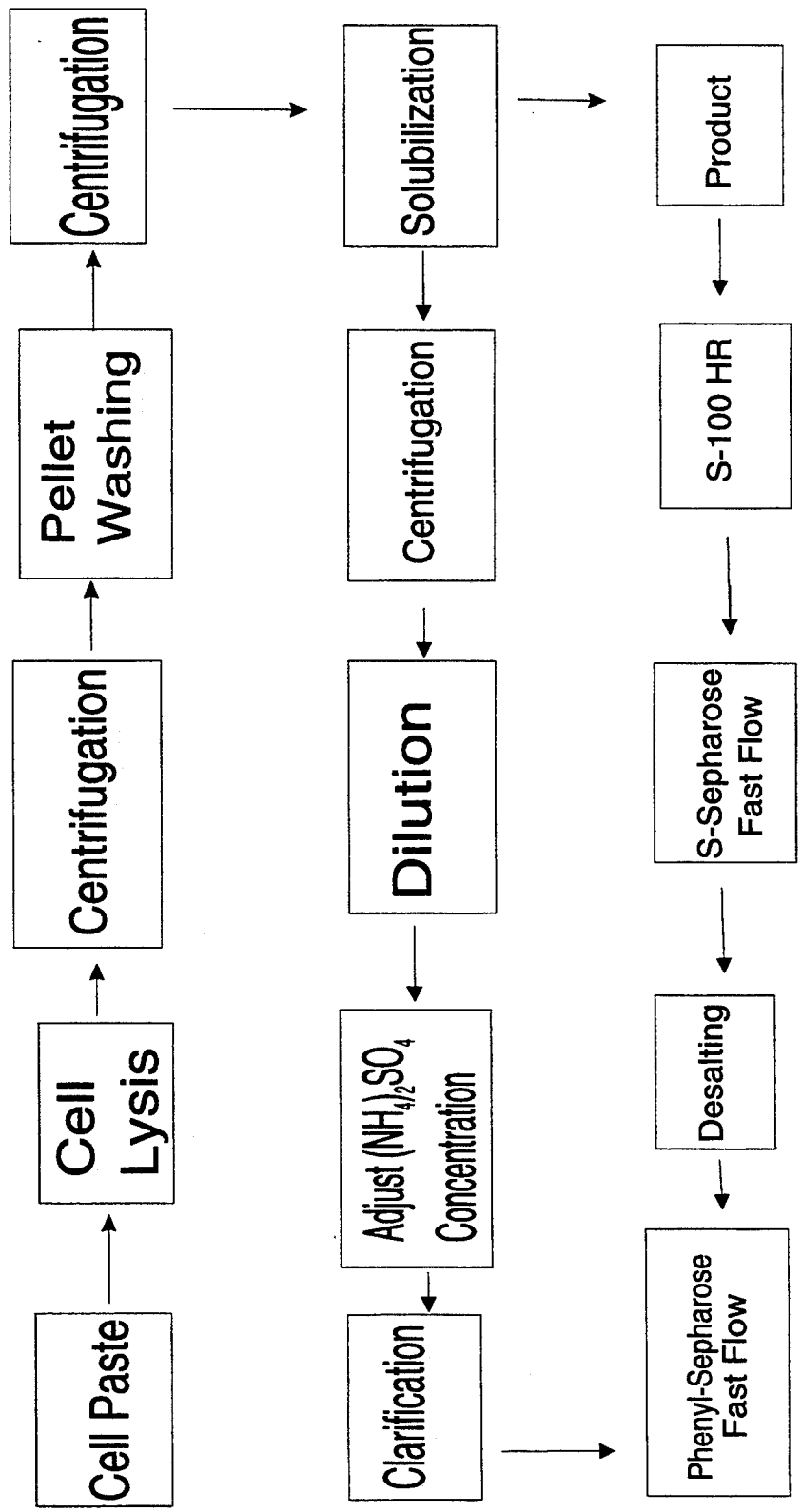
FIG. 9A shows a purification scheme for -22aa IL-6 SSCC.

Example 11B. Alternative Purification and Characterization of pKK-22aa IL-6 SSCC a. A flow diagram of an alternative purification process is provided in FIG. 9A. Briefly, the recombinant cell lysate pV3-22aa IL-6 SSCC or pKK-22aa IL-6 SSCC is prepared by resuspending the cell paste from Example 6 or 7, respectively, in 20 mM Tris-HCl pH 8.0, 50 mM NaCl, 10 mM EDTA, 0.1 mM PMSF (TNE buffer) and incubating with lysozyme for 30 minutes at 4° C. Following the incubation with lysozyme, the suspension is homogenized on ice and then centrifuged at $5000 \times g$ for 30 minutes. The resulting pellet is washed twice with TNE buffer containing 0.5% Triton X-100 and the supernatants discarded. The pellet containing -22aa IL-6 SSCC inclusion bodies is resuspended in 6M guanidine hydrochloride, 1 mM EDTA, 50 mM Tris-HCl pH 8.5 and incubated for 2 hours at room temperature. The extract is then clarified by centrifugation at $10,000 \times g$ for 60 minutes.

b. The solubilized -22aa IL-6 SSCC extract is refolded by diluting with 20 mM Tris-HCl pH 8.5, 100 mM NaCl, 1 mM EDTA and slowly mixing for 20-24 hours at 4° C. The diluted extract is then adjusted to 45% saturation with solid ammonium sulfate and contaminants are allowed to precipitate out for 2 hours at 4° C. The extract is then clarified for chromatography by tangential flow microporous filtration through a 0.45 u cutoff membrane.

c. The clarified extract is loaded onto a Phenyl-Sepharose Fast Flow column (Pharmacia) equilibrated with 1.8M $(NH_4)_2SO_4$, 20 mM sodium phosphate ph 7.0. The sample is loaded at a flow rate of 150 cm $hour^{-1}$ and eluted at 95 cm $hour^{-1}$ with a linear gradient of 20 mM sodium phosphate pH 7.0.

d. The Phenyl-Sepharose pool is desalted on a Sephadex G-25 column (Pharmacia) and then loaded onto a S-Sepharose Fast Flow column equilibrated with 20 mM citrate-phosphate pH 6.0. The sample is loaded at a flow rate of 200 cm $hr^{-1}$ and then eluted at 120 cm $hr^{-1}$ with a complex gradient of 500 mM NaCl in a citrate-phosphate, buffer pH 6.0.

e. The S-Sepharose FF pool is loaded onto a Sephacryl-100HR column (Pharmacia) previously equilibrated with a phosphate-buffered saline pH 7.4. The column is eluted at a flow rate of 24 cm $hr^{-1}$ and the IL-6 functions are pooled, sterile filtered, and frozen until further use.

The purification scheme described above provides active -22aa IL-6 SSCC at >95% purity as determined by SDS-PAGE and HPLC analysis. The final yield of IL-6 from this process is 25-40% with larger scales resulting in higher yields.

Example 11C. Large Scale Purification of -22aa IL-6 SSCC

The recombinant cell lysate -22aa IL-6 SSCC is prepared by resuspending the *E. coli* cell paste from Example 6 or Example 7 in 20 mM Tris-HCl pH 8.0, 50 mM NaCl, 10 mM EDTA, 0.1 mM PMSF (TNE buffer) and incubating with lysozyme for 30 minutes at 4° C. Following incubation with lysozyme, the suspension is homogenized on ice and then centrifuged at $5000 \times g$ for 30 minutes. The resulting pellet is washed by centrifugation $2 \times$ with TNE buffer containing 0.5% Triton X-100 and the supernatants discarded. The pellet containing the -22aa IL-6 SSCC inclusion bodies is resuspended in 6M guanidine-HCl, 1 mM EDTA, 50 mM Tris-HCl pH 8.5. The resuspended pellet is stirred 18-20 hrs at 4° C. and then clarified by centrifugation at $10,0000 \times g$ for 60 minutes.

The solubilized -22aa IL-6 SSCC is refolded by dilution with 20 mM Tris-HCl pH 8.5, 100 mM NaCl, 1 mM EDTA, 0.1 mM PMSF. The pH is adjusted with 2M Tris if necessary and then slowly mixed for 20-24 hrs at 4° C. The refolded extract is then clarified by filtration through a 1 um filter and desalted into 20mM Tris-HCl pH 8.5 by tangential flow ultrafiltration (Pellicon System, Millipore) with a 10 kd cutoff membrane. The conductivity of the refolded extract is <3.0 mS/cm prior to chromatography.

The desalted extract is loaded onto a S-Sepharose Fast Flow column (5 cm $\times$ 10 cm; Pharmacia) equilibrated with 20 mM Tris-HCl pH 8.5. The column is eluted at a flow rate of 34 ml/min with a multi-step gradient of 20 mM Tris-HCl pH 8.5, 500 mM NaCl. The -22aa IL-6 SSCC containing fractions are pooled and adjusted to 1.8M ammonium sulfate.

The S-Sepharose pool is loaded onto a Phenyl-Sepharose HP column (2.6 cm×10 cm; Pharmacia) equilibrated with 20 mM Tris-HCl pH 8.5, 1.8M ammonium sulfate. The column is eluted at 8 ml/min with a complex gradient of 20 mM Tris-HCl pH 8.5.

The Phenyl-Sepharose fractions containing >95% pure -22aa IL-6 SSCC are pooled and formulated into phosphate-buffered saline pH 7.4, 5% mannitol at 250 ug -22aa IL-6 SSCC/ml. The formulated material is sterile filtered and then 1 ml aliquots are dispensed into glass serum vials and lyophilized. Lyophilized vials are stored at −20° C.

Example 12. Bioassay of IL-6

Two standard bioassays are used for screening the presence of IL-6 and IL-6 muteins. These include the proliferation of an IL-6 requiring murine hybridcma cell line (B-9) and IL-6 stimulation of IgM production in an EBV-transformed B cell line (SKW 6.4); see Heile et al, Eur. J. Immunol. 18, 1535 (1988) and Saiki et al, Eur. J. Immunol 13, 31–44 (1983), respectively. In both assays, bacterial-derived IL-6 from Boerhinger Mannheim (BM) and full length cysteine-free IL-6 (IL-6 SSSS) prepared in accordance with the method described in WO90/06370 are used as the standards. Two samples of -22aa IL-6 SSCC, R- 4 28 and R-4 29, are assayed for activity and compared with the standards. R-4 28 and R-4 29 are purified samples from a reverse phase run of clone pKK-22 IL-6 SSCC (Example 9A).

Figure 10:
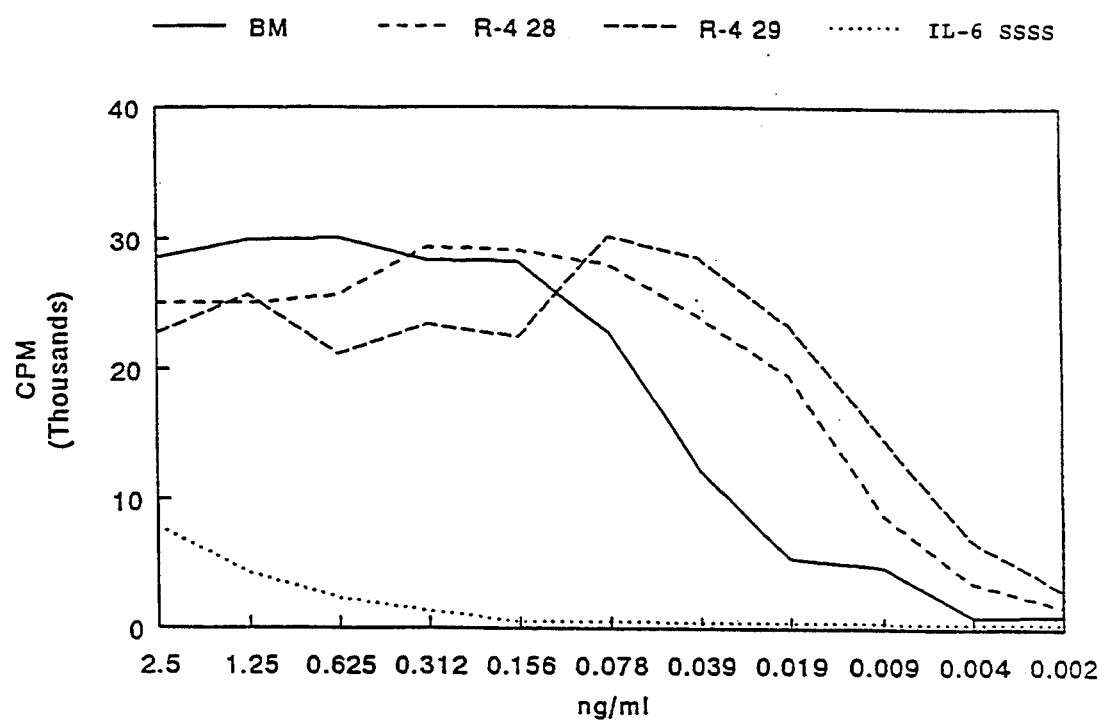
FIG. 10 shows the results of the B9 proliferation assay described in Example 12.

In the B9 assay, samples are diluted to a concentration of 2.5 ng/ml and serially diluted in a 96-well plate. Two thousand B9 cells are added to each well and incubated for 3 days at 37° C. Cells are pulsed with 2 uCi/well of tritiated thymidine for 18 hours, harvested onto a fiber glass filter, and counted. The results are shown in FIG. 10.

Figure 11:
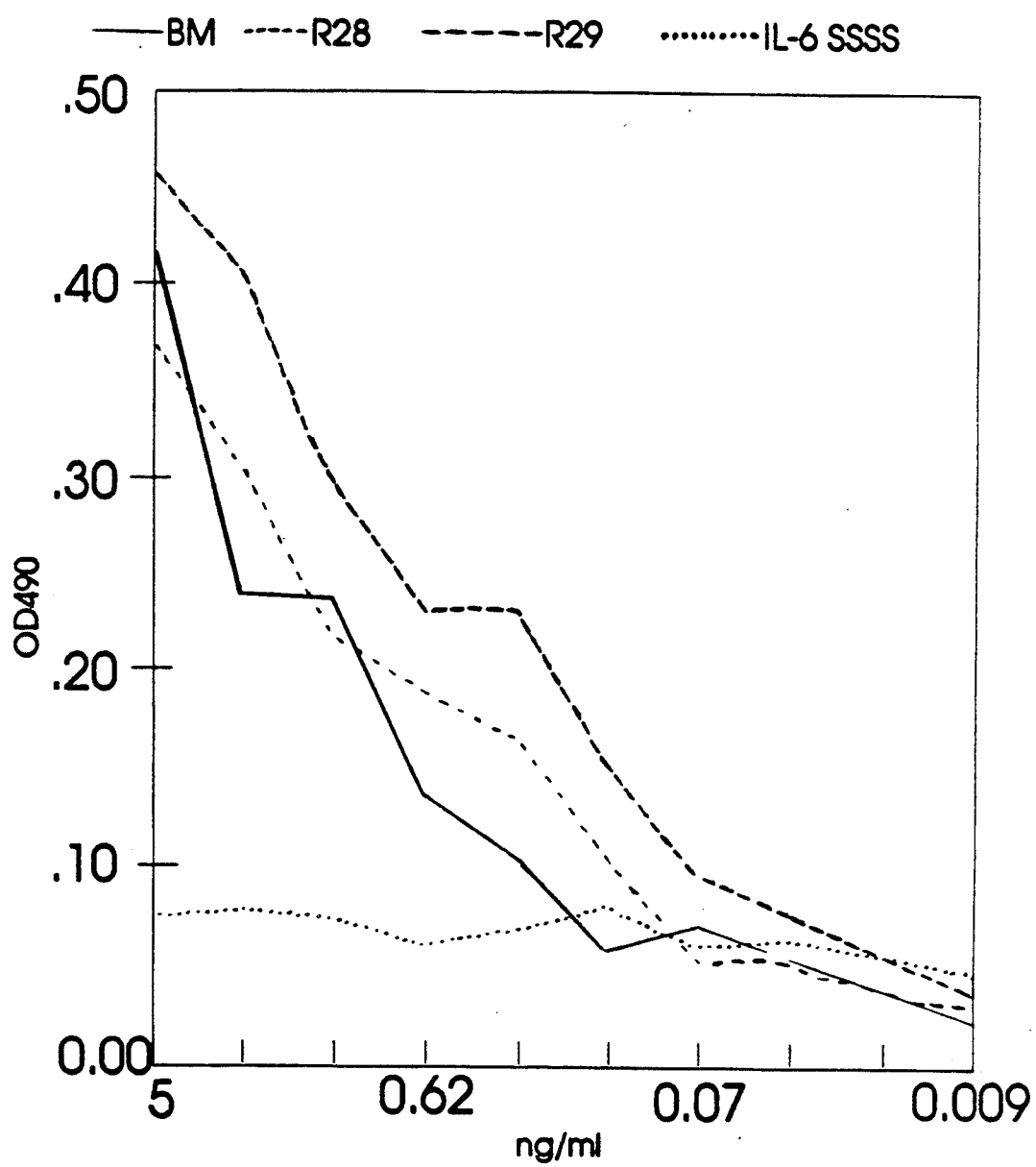
FIG. 11 shows the SKW6.4 human IgM production assay described in Example 12.

In the SKW6.4 assay, samples are diluted to a concentration of 5 ng/ml and serially diluted in a 96-well plate. Five thousand SKW6.4 cells are added per well and incubated for 4 days. A sandwich ELISA is used to determine IgM production. A polyclonal goat anti-human antibody is used to coat 96 well Immulon plates. Aliquots of the cell supernatants is diluted 1:1 with 1% BSA and incubated for one hour at 37° C. IgM production is determined using goat anti-human Ig conjugated to horseradish peroxidase and TMB. The results are shown in FIG. 11.

The results of both assays indicate that R-4 28 and R-4 29 exhibit at least comparable activity when compared to IL-6 from Boerhinger Mannheim.

Example 13. Fusion Protein Containing trpE DNA Sequence Followed by Xa Cleavage Site and -22aa IL-6 SSCC Fusion Vector.

a. The -22aa IL-6 SSCC can also be expressed as a fusion protein by methods similar to those described above. The fusion protein contains the product of the trpE gene, anthranilate synthase, at the N-terminal end, followed by an enzymatic cleavage site, followed immediately by the -22aa IL-6 SSCC, and is expressed by a new recombinant plasmid ptrpE/Xa/-22aa IL-6 SSCC. To prepare this plasmid, the pTrpE/EK/cfIL6 vector described in Section 5.10.1. of PCT application WO90/06370 is digested with KpnI in the following buffer: 20 mM Tris-HCl pH 7.4, 5 mM MgCl2 and 50 mM KCl. pTrpE/EK/cfIL-6 was deposited in the American Type Culture Collection, Rockville, Md. on Nov. 17, 1989 (accession number 68180). The sequence of the HindIII/KpnI fragment is shown as FIG. 12. After two hours, 50 mM NaCl is added as well as HindIII. The vector is digested with 20 units of each enzyme per 20 μg of plasmid at 37° C. for two hours. The large 3.7 Kb fragment is isolated by electro-elution, and is called Sequence J. Alternatively, the pATH 23 expression vector can be used and digested with the same enzyme as above. pATH 23, which is described by Dieckmann and Tzagoloff in J. Biol. Chem. 260, 1513–1520 (1985), is an ampicillin-resistance plasmid containing a gene that encodes the amino-terminal 337 amino acids of trpE (anthranilate synthase component I) adjacent to, and in reading frame at its 3' end with, a polylinker containing a HindIII site. A general description of the trpE operon may be found in Miller and Reznikoff, eds., The Operon, Cold Spring Harbor Laboratory, pp. 263–302 (1978). Other sources of DNA that encode all or part of trpE and lacZ are readily available. Such other sources may be found, for example, in Pouwels, et al., Cloning Vectors, A Laboratory Manual, Elsevier, 1985. Suitable trpE sequences may be isolated from plasmids having the following identifying codes in the Pouwels, et al. manual: I-A-ii-3 (pDF41 and 42), I-A-iv-23 (pRK353), I-B-ii-4 (pMBL24), I-B-ii-1 (ptrpED-5-1), I-D-i-3 (pEP70-pEP75), and I-D-i-4 (pEP165 and pEP168).

b. The pKK-22aa IL-6 SSCC is digested with the enzymes ClaI and Kpn I in the following buffer: 20 mM Tris-HCl pH 7.4, 5 mM MgCl2 and 50 mM KCl, and the 0.49 Kb fragment is isolated by electro-elution. This fragment, which is called Sequence K, encodes an IL-6 fragment that starts at the 26th amino acid of the native, mature protein and continues through to the natural methionine carboxy-terminal amino acid of IL-6. When this fragment is ligated to the oligonucleotide below, the 23rd, 24th and 25th amino acids of IL-6 are encoded immediately upstream of this fragment and a Xa cleavage site is encoded directly upstream of the 23rd amino acid.

c. A synthetic oligonucleotide is prepared which contains overlapping HindIII and ClaI sites and encodes a sequence of amino acids containing an Xa cleavage site (Ile-Glu-Gly-Arg) followed by the 23rd, 24th, and 25th amino acids of IL-6 (Ser-Glu-Arg . . . ).

The sequence of the oligonucleotide (SEQ ID NO: 20 and SEQ ID NO: 21) is:

```
5' AGCTTGATCAGGCGGATCCGGAAGGTGGTAGC
3'   ACTAGTCCGCCTAGGCCTTCCACCATCG

ATCGAAGGTCGTTCCGAACGTAT 3'
  TAGCTTCCAGCAAGGCTTGCATAGC 5'
``` d. The above oligonucleotide (1 pmole) is ligated to 1 pmole of Sequence J and 3 pmoles of Sequence K. Ten ul of the ligation reaction mixture is transformed into competent E. coli HB101 cells. The amp$^R$ clone derived from this ligation is called pTrpE Xa -22aa IL-6 SSCC and contains the TrpE gene, followed by a factor Xa cleavage site, followed immediately by the 23rd amino acid of IL-6 (Ser-Glu-Arg . . . ). Following induction with 3-beta-indoleacrylic acid (IAA), the HB101 cells express an IL-6 mutein that lacks the N-terminal 22 amino acid residues and contains serine residues at the positions corresponding to amino acid residues 45 and 51 of full length, native IL-6. The TrpE/Xa/-22aa IL-6

SSCC mutein fusion protein is cleaved with factor Xa and the mutein is purified in accordance with the procedure described by Asagoe in Biotechnology 6, 806-809 (1988).

Example 13A. Additional IL-6 Muteins

The following additional muteins of the invention are prepared by following the protocols of Examples 1-13 with, at most, minor, routine modifications: IL-6 AACC, -ASCC, -SACC, -GGCC, -SGCC, -GSCC, -DRCC, -RDCC, -TTCC, -ATCC, -TSCC, -PPCC, -PGCC.

Example 14A. IL-6 Mutein Variants with Modified N-Terminal End. MetGly -2aa IL-6 CCCC and MetGly -2aa IL-6 SSSS Variants of IL-6 muteins containing changes in the sequence of mature, native IL-6 other than those described above are prepared from starting materials described in this example by known methods. DNA is sequenced by the chain-termination method with a commercially available kit (Sequenase Kit; United States Biochemical Corp. Cleveland, Ohio). All DNA manipulations are performed according to standard procedures.

In one example, the first two amino acids of mature, native IL-6, AlaPro, are replaced by MetGly. The procedure for doing so begins by providing two plasmids containing DNA sequences that encode IL-6 variants. Both DNA sequences encode variants that contain MetGly as the first two amino acid residues instead of AlaPro. One DNA sequence encodes cysteine residues at the positions that correspond to positions 45, 51, 74 and 84 of mature, native IL-6. This variant is called MetGly -2aa IL-6 CCCC. The other DNA sequence contains a serine residue at each of these positions. This variant is called MetGly -2aa IL-6 SSSS. Suitable plasmids for the serine-containing and cysteine-containing IL-6 variants are p365 and p469, respectively.

The preparation of p365 is described by Jambou et al. in Proc. Natl. Acad. Sci. USA 85, 9426-9430 (1988). Briefly, a DNA sequence encoding an IL-6 variant wherein MetGly replaces AlaPro as the first two amino acids and all four native cysteine residues are replaced by serine residues is assembled from 22 synthetic oligonucleotides and initially cloned into a modified pBS M13+ cloning vector (Stratagene, La Jolla, Calif.). The stop codon of the natural gene is converted to a serine codon by cassette mutagenesis with synthetic oligonucleotides to produce the plasmid p365.

The variant IL-6 gene in p365 is subcloned into the expression vector p340 as described previously by Jambou et al., Id. The p340 vector is constructed by replacement of the lambda $P_B$ promoter of the expression vector pJG200 described by Germino et al. in Proc. Natl. Acad. Sci. USA 81, 4692 (1984) with the P-trc promoter of pKK233-2 (Pharmacia LKB Biotechnology, Inc., Piscataway, N.J.). A synthetic minicistron is inserted into the NcoI site immediately downstream of the P-trc promoter. The sequence of this minicistron (SEQ ID NO: 22), beginning with the initiating methionine and extending to the initiating methionine of the variant IL-6 gene, is 5'-ATGTATCGAT-TAAATAAGGAGGAATAACCATG-3'. The gene encoding the cysteine-containing IL-6 variant MetGly -2aa IL-6 CCCC is constructed by replacement of the EcoRV to StuI fragment of the serine-containing variant, MetGly -2aa IL-6 SSSS in p365 with a fragment composed of six synthetic oligonucleotides. This fragment is identical in sequence to the original EcoRV to StuI fragment, except that the codons corresponding to the four cysteine codons of native IL-6 are changed from serine codons back to the wild type cysteine codons, i.e., in the 5'-3' direction, TGC, TGC, TGT, and TGT. After sequence verification, the DNA encoding the cysteine-containing IL-6 variant, MetGly -2aa IL-6 CCCC, in the resulting plasmid, p463, is removed and inserted into the p340 expression vector to create the plasmid p478.

Example 14B. Construction of DNA Encoding IL-6 Mutein Variants MetGly -2aa IL-6 SSCC by Recombinant Circle PCR.

Genes in which individual pairs of cysteine codons are replaced by pairs of serine codons are constructed by a modification of the recombinant circle polymerase chain reaction method as described by Jones et al. in BioTechniques 8, 178-183 (1990). The plasmids p365 and p469, which contain the genes encoding MetGly -2aa IL-6 SSSS and MetGly -2aa IL-6 CCCC respectively, are used in the procedure.

The plasmid p365 is described above. Construction of p469 was carried out by assembling a fragment out of synthetic oligonucleotides analogous to that in p334. See Jambou et al., Proc. Natl. Acad. Sci. USA 85, 9426 (1988). This was cloned into modified pBS vector to produce p463. The fragment from p463 was used to replace the analogous fragment (RV-Stu) in p365. The resulting vector, which is analogous to p365 except that the gene encodes wild type cysteines, is called p469. The gene from this vector was cloned into an expression vector to produce p478, which was the vector used to express rIL-6 described in FIG. 1 of Snouwaert et al., J. Immunol., 146, 585-591 (1991).

As described by Snouwaert et al. in J. Biol. Chem. 266, 23097-23102 (1991), p469 and p365 are each amplified with two separate primer sets. One primer set, designated a, is used to amplify the entire length of each plasmid, with the exception of a region encompassing the positions corresponding to codons 45 and 51 of native, mature IL-6. These codons represent serine residues in the case of p365 and cysteine residues in the case of p469. The products of this type of reaction are designated as p365a or p469a, depending on the template used in the reaction.

In a similar manner, p365 and p469 are used as templates in a second round of PCR using primer set b to produce products p365b and p469b. These amplification products include the entire length of each plasmid, with the exception of a region encompassing the positions corresponding to codons 74 and 84 of native, mature IL-6.

After gel purification, products p365a and p469b are combined, denatured, and annealed to produce recombinant circles with two single stranded gaps. The single-stranded DNA across the first gap encodes cysteine residues at positions corresponding to codons 45 and 51 from p469b. The single-stranded DNA across the second gap encodes serine residues at positions corresponding to codons 74 and 84 from p365a. After transformation into *E. coli*, these gapped circles are repaired to produce p642, which carries DNA encoding an IL-6 mutant variant, MetGly -2aa IL-6 CCSS, in which the cysteine residues at positions 74 and 84 are replaced by serine residues. MetGly -2aa IL-6 CCSS is useful for comparison purposes, but is not a mutein variant in accordance with the present invention.

In an analogous manner, p365b and p469a are annealed and transformed to produce p643, which encodes an IL-6 mutant variant, MetGly -2aa IL-6 SSCC, in which the cysteine residues at positions 45 and 51 are replaced by serine residues. MetGly -2aa IL-6 SSCC is a mutein variant of the present invention.

Example 14C. Mutant Variants Containing Alanine and Charged Amino Acids at the Native Cysteine Positions of IL-6 Prepared by Directed Mutagenesis.

Mutein variants of IL-6 in which alanines or charged residues (aspartic acid and arginine) are present at positions corresponding to two or all four cysteines of native IL-6 are constructed from MetGly -2aa IL-6 CCCC using the T7-GEN ™ Mutagenesis kit (United States Biochemicals, Cleveland, Ohio) according to instructions provided with the kit. To improve the yield of single-stranded DNA needed for the mutagenesis reaction, the DNA encoding MetGly -2aa IL-6 CCCC is subcloned between the HindIII and PvuI sites of M13 mp19. Single-stranded DNA is produced using standard procedures, such as those described by Greenstein in Current Protocols in Molecular Biology (Ausubel et al., eds) pages 1.15.2–1.15.3, John Wiley & Sons, New York (1989). Mutagenic oligonucleotides are used to mutate single pairs of cysteines. Mutants in which both pairs of cysteines are replaced by alanines or charged residues (aspartic acid and arginine) are produced by two consecutive rounds of mutagenesis.

Following sequence verification by dideoxy sequencing, DNA encoding each of the IL-6 variants are subcloned into the p340 expression vector, which is described in Example 14A. These vectors, which are precursors of p478 (see Example 14A), allow high level expression of IL-6 variants as beta-galactosidase fusion proteins. The fusion protein has an N-terminal beta-galactosidase fragment followed by a collagenase cleavage site followed by the IL-6 mutant variant.

Example 14D. Expression, purification and quantitation of IL-6 Mutein variants.

Expression vectors containing genes for IL-6 variants (Examples 14B and 14C) are transformed into E. coli JM101. Single ampicillin-resistant colonies are used to innoculate 10 ml broth cultures, and allow expression of the IL-6 mutein variants as beta-galactosidase fusion proteins is induced by addition of isopropyl beta-D-thiogalactopyranoside (IPTG). When beta-galactosidase activity reaches a maximum, the bacteria are pelleted by centrifugation and stored at −20° C. Bacteria are resuspended and lysed by freezing and thawing following lysozyme treatment. Lysate is sonicated to reduce viscosity, and the fusion protein, along with other insoluble material, is pelleted by centrifugation. The pellet is washed to remove soluble contaminants, and the fusion protein is solubilized in 2% sodium lauroyl sarcosine. Insoluble contaminants are removed by centrifugation, and the fusion protein is further purified by two rounds of selective ammonium sulfate precipitation. Before bioassay or quantitation, the IL-6 variants are cleaved from beta-galactosidase with collagenase. Proteins are quantitated by denaturing polyacrylamide gel electrophoresis under reducing conditions followed by Coomassie staining and scanning laser densitometry.

For use in binding studies, the IL-6 mutant variants are purified to apparent homogeneity essentially by known methods. Briefly, E. coli transformed with the p478 variants are grown in a 10 liter batch culture, induced with IPTG, and pelleted when beta-galactosidase activity reaches a maximum. The fusion protein is partially purified essentially as described above, except that volumes are scaled up appropriately. After treatment with collagenase, most of the contaminating beta-galactosidase is removed by selective ammonium sulfate precipitation. The IL-6 mutein variants are precipitated by increasing the ammonium sulfate concentration, and the resulting precipitate is collected as a floating pellicle after centrifugation. The pellicle is resuspended in 0.1% trifluoroacetic acid/30% acetonitrile and the IL-6 mutein variants are separated from the remaining contaminants by reverse-phase high performance liquid chromatography. Fractions containing the IL-6 mutein variants are lyophilized and resuspended in phosphate buffered saline containing 0.01% (v/v) Tween-20. The concentration of purified IL-6 mutein variants is determined as described above for partially purified protein.

Example 14E. Additional Mutein Variants

In addition to those described above, the following mutein variants, in which the first two amino acids of native IL-6, AlaPro, are replaced by MetGly and either the first pair of cysteine residues (positions 45 and 51), the second pair of cysteine residues (positions 74 and 84), or both pairs of cysteine residues are replaced by either one or two pairs of alanine (A) residues or by one or two pairs of oppositely charged amino acids (aspartic acid (D) and arginine (R)) are prepared by methods analogous to those described in Example 14A–14D. Using nomenclature analogous to that described above, the following mutant variants are prepared: MetGly -2aa IL-6 AAAA, MetGly -2aa IL-6 DRDR, MetGly -2aa IL-6 AACC, MetGly -2aa IL-6 DRCC, MetGly -2aa IL-6 CCAA, MetGly -2aa IL-6 CCSS and MetGly -2aa IL-6 CCDR.

Example 15. Bioassays

Bioassays are conducted in accordance with Snouwaert et al, J. Immunol., 146, 585–591 (1991). Briefly, cells are treated with varying concentrations of IL-6 mutein variants in 96 well microtiter plates. For each mutant, two or three independent protein preparations are tested in duplicate in each bioassay. Hybridoma growth factor activity is determined by measuring proliferation of a mouse-mouse hybrid cell line (7TD1) using colorimetric determination of hexosaminidase levels. B cell differentiation activity is determined by measuring IL-6 stimulated secretion of IgM from a human EBV transformed B cell line (SKW6.4). IgM is quantitated using a sandwich enzyme-linked immunosorbent assay (ELISA). Hepatocyte stimulation activity is determined by measuring IL-6 stimulated secretion of fibrinogen from human (HEP 3B2) and rat (FAZA 967) hepatoma cells. Fibrinogen is quantitated using a sandwich ELISA specific for human or rat fibrinogen.

Quantition of biologic activities is carried out by known methods. Briefly, activity in the hybridoma growth assay is defined as the concentration of IL-6 or IL-6 mutant variant needed to cause half-maximal proliferation, while activity in the hepatocyte stimulation and B-cell differentiation assays is defined as the concentration of IL-6 needed to cause doubling or quadrupling of secretion of fibrinogen or IgM, respectively. For calculation of activities, dose response curves are plotted on a semilogarithmic scale, and a computer program is used to fit the approximately linear portion of each curve with a second order polynomial. Activities for each assay are expressed as a percentage of the activity of non-mutated rIL-6 in the same assay. The results are shown in Table 4 and FIG. 14.

TABLE 4

Biologic activities[a] of IL-6 mutant variants as percent activity of MetGly -2aa IL-6 CCCC

| Mutant Variant[b] | FAZA 967[c] | 7TD1[c] | HEP 3B2[c] | SKW6.4[c] |
|---|---|---|---|---|
| CCCC | 100 | 100 | 100 | 100 |
| AAAA | 52 ± 12 | 5.7 ± .4 | 0.8 ± .05 | 0.3 ± .08 |
| SSSS | 22 ± 2.5 | 1.07 ± .17 | 0.07 ± .007 | 0.02 ± .005 |
| DRDR | 8.8 ± 1.6 | 0.8 ± .07 | <0.1 | <0.05 |
| AACC | 92 ± 9.7 | 90 ± 4.7 | 78 ± 10 | 109 ± 11 |
| SSCC | 128 ± 6.8 | 66 ± 9.0 | 121 ± 9.0 | 103 ± 11 |
| DRCC | 78 ± 11 | 101 ± 9.4 | 99 ± 6.0 | 90 ± 14 |
| CCAA | 67 ± 11 | 20 ± 4.7 | 2.4 ± .14 | 1.1 ± .21 |
| CCSS | 39 ± 8.5 | 9.0 ± 3.3 | 0.7 ± .14 | 0.14 ± .03 |
| CCDR | 20 ± 6.2 | 3.5 ± .64 | 0.3 ± .08 | 0.06 ± .008 |

[a]Activities of all mutants are given as a percentage of the activity ± SEM of rIL-6, which has been assigned an activity of 100% in all of the bioassays. For mutants in which activity was too low to quantitate accurately, activity is given as <c, where c represents the lowest level of activity which can be accurately quantitated in a given assay.
[b]MetGly -2aa IL-6 XXXX variants are named as described in Example 14E.
[c]Activities in the four bioassays were calculated as described in Example 15.

Supplemental Enablement

The invention as claimed is enabled in accordance with the specification and readily available references and starting materials. Nevertheless, the following cell lines are available in the American Type Culture Collection, Rockville, Md. in order to facilitate the making and using of the invention:

pBgal/EK/cfIL-6 (accession number 68187, deposited Nov. 30, 1989)

pTrpE/EK/cfIL-6 (accession number 68180, deposited Nov. 17, 1989)

These deposits were made under the provisions of the Budapest Treaty on the International Recognition of the Deposit of Microorganisms for the Purposes of Patent Procedure and the regulations thereunder (Budapest Treaty). This assures maintenance of a viable culture for 30 years from date of deposit. The organisms will be made available by ATCC under the terms of the Budapest Treaty, and subject to an agreement between Applicants and ATCC, which assures unrestricted availability upon issuance of the pertinent U.S. patent. Availability of the deposited strains is not to be construed as a license to practice the invention in contravention of the rights granted under the authority of any government in accordance with its patent laws.

In addition, the following brochures containing useful protocols and information are available in the file history of this specification.

"Altered Sites in vitro Mutagenesis System Technical Manual" Promega Corporation.

---

What we claim is:

1. A mutein of IL-6 wherein the cysteine residues at positions, or at positions corresponding to positions, 45 and 51 of native human IL-6 have each been replaced by other amino acids, and the cysteine residues at positions, or at positions corresponding to positions, 74 and 84 have been retained.

2. The mutein of claim 1 wherein the other amino acids at positions, or at positions corresponding to positions, 45 and 51 are neutral amino acids.

3. The mutein of claim 1 wherein the other amino acids at positions, or at positions corresponding to positions, 45 and 51 are both serine residues.

4. A mutein of IL-6 wherein the cysteine residues at positions, or at positions corresponding to positions, 45 and 51 of native human IL-6 have each been replaced by serine residues, and the cysteine residues at positions, or at positions corresponding to positions, 74 and 84 have been retained.

5. A mutein of IL-6 wherein the cysteine residues at positions, or at positions corresponding to positions, 45 and 51 of native human IL-6 have each been replaced by other amino acids; the cysteine residues at positions, or at positions corresponding to positions, 74 and 84 have been retained; and from 1 to 28 N-terminal amino acids are lacking.

6. The mutein of claim 5 wherein the other amino acids at positions, or at positions corresponding to positions, 45 and 51 are neutral amino acids.

7. The mutein of claim 5 wherein the other amino acids at positions, or at positions corresponding to positions, 45 and 51 are both serine residues.

8. The mutein of claim 5 wherein the 22 N-terminal amino acids are lacking.

9. The mutein of claim 5 wherein the N-terminal alanine residue is lacking.

10. A mutein of IL-6 wherein the cysteine residues at positions, or at positions corresponding to positions, 45 and 51 of native IL-6 have each been replaced by serine residues; the cysteine residues at positions, or at positions corresponding to positions, 74 and 84 have been retained; and the 22 N-terminal amino acids are lacking.

* * * * *

SEQUENCE LISTING ( 1 ) GENERAL INFORMATION:

( i i i ) NUMBER OF SEQUENCES: 14

( 2 ) INFORMATION FOR SEQ ID NO:9:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:9:

CATGGCTCCG GTTCCG          16

( 2 ) INFORMATION FOR SEQ ID NO:10:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:10:

CCTGGCGGAA CCGGAGC          17

( 2 ) INFORMATION FOR SEQ ID NO:11:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:11:

Met Ala Pro Val Pro
1               5

( 2 ) INFORMATION FOR SEQ ID NO:12:

(i) SEQUENCE CHARACTERISTICS:
    (A) LENGTH: 15 base pairs
    (B) TYPE: nucleic acid
    (C) STRANDEDNESS: single
    (D) TOPOLOGY: linear (xi) SEQUENCE DESCRIPTION: SEQ ID NO:12:

```
CATGTCCGAA CGTAT                                                         15
```

(2) INFORMATION FOR SEQ ID NO:13:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (xi) SEQUENCE DESCRIPTION: SEQ ID NO:13:

```
CGATACGTTC GGA                                                           13
```

(2) INFORMATION FOR SEQ ID NO:14:

(i) SEQUENCE CHARACTERISTICS:
        (A) LENGTH: 81 base pairs
        (B) TYPE: nucleic acid
        (C) STRANDEDNESS: single
        (D) TOPOLOGY: linear (xi) SEQUENCE DESCRIPTION: SEQ ID NO:14:

```
CCGAAGATGG CTGAAAAGA TGGATGTTTT CAATCTGGAT TCAATGAGGA AACTTGTCTG         60

GTGAAAATCA TCACAGGCCT T                                                  81
```

(2) INFORMATION FOR SEQ ID NO:15:

(i) SEQUENCE CHARACTERISTICS:
        (A) LENGTH: 62 base pairs
        (B) TYPE: nucleic acid
        (C) STRANDEDNESS: single
        (D) TOPOLOGY: linear (xi) SEQUENCE DESCRIPTION: SEQ ID NO:15:

```
AGCTTGGTAC CACACCATGG ATGTATATCT CCTTCTTAAA GTTAAACAAA ATTATTTCTA        60

GG                                                                       62
```

(2) INFORMATION FOR SEQ ID NO:16:

(i) SEQUENCE CHARACTERISTICS:
        (A) LENGTH: 62 base pairs
        (B) TYPE: nucleic acid
        (C) STRANDEDNESS: single
        (D) TOPOLOGY: linear (xi) SEQUENCE DESCRIPTION: SEQ ID NO:16:

```
AATTCCTAGA AATAATTTTG TTTAACTTTA AGAAGGAGAT ATACATCCAT GGTGTGGTAC        60

CA                                                                       62
```

(2) INFORMATION FOR SEQ ID NO:17:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (xi) SEQUENCE DESCRIPTION: SEQ ID NO:17:

```
CATGGTTTAA ACCTCCTTAC TAATCGATAC CCTTTTACG TGAACTTG                      48
```

( 2 ) INFORMATION FOR SEQ ID NO:18:

( i ) SEQUENCE CHARACTERISTICS:
( A ) LENGTH: 48 base pairs
( B ) TYPE: nucleic acid
( C ) STRANDEDNESS: single
( D ) TOPOLOGY: linear ( x i ) SEQUENCE DESCRIPTION: SEQ ID NO:18:

AATTCAAGTT CACGTAAAAA GGGTATCGAT TAGTAAGGAG GTTTAAAC     48

( 2 ) INFORMATION FOR SEQ ID NO:19:

( i ) SEQUENCE CHARACTERISTICS:
( A ) LENGTH: 69 base pairs
( B ) TYPE: nucleic acid
( C ) STRANDEDNESS: single
( D ) TOPOLOGY: linear ( x i ) SEQUENCE DESCRIPTION: SEQ ID NO:19:

TGCCAGTGCT TCTTTACTGC TTTCTGCCAT GTTACTCTTG TTAGCGGTCT CTTTTCTCAG     60

CGCTGATAT     69

( 2 ) INFORMATION FOR SEQ ID NO:20:

( i ) SEQUENCE CHARACTERISTICS:
( A ) LENGTH: 55 base pairs
( B ) TYPE: nucleic acid
( C ) STRANDEDNESS: single
( D ) TOPOLOGY: linear ( x i ) SEQUENCE DESCRIPTION: SEQ ID NO:20:

AGCTTGATCA GGCGGATCCG GAAGGTGGTA GCATCGAAGG TCGTTCCGAA CGTAT     55

( 2 ) INFORMATION FOR SEQ ID NO:21:

( i ) SEQUENCE CHARACTERISTICS:
( A ) LENGTH: 53 base pairs
( B ) TYPE: nucleic acid
( C ) STRANDEDNESS: single
( D ) TOPOLOGY: linear ( x i ) SEQUENCE DESCRIPTION: SEQ ID NO:21:

CGATACGTTC GGAACGACCT TCGATGCTAC CACCTTCCGG ATCCGCCTGA TCA     53

( 2 ) INFORMATION FOR SEQ ID NO:22:

( i ) SEQUENCE CHARACTERISTICS:
( A ) LENGTH: 32 base pairs
( B ) TYPE: nucleic acid
( C ) STRANDEDNESS: single
( D ) TOPOLOGY: linear ( x i ) SEQUENCE DESCRIPTION: SEQ ID NO:22:

ATGTATCGAT TAAATAAGGA GGAATAACCA TG     32